United States Patent
Rastgaar et al.

(10) Patent No.: US 9,849,003 B2
(45) Date of Patent: Dec. 26, 2017

(54) SYSTEM FOR POWERED ANKLE-FOOT PROSTHESIS WITH ACTIVE CONTROL OF DORSIFLEXION-PLANTARFLEXION AND INVERSION-EVERSION

(71) Applicant: Mayo Foundation for Medical Education and Research, Rochester, MN (US)

(72) Inventors: Mo Rastgaar, Houghton, MI (US); Evandro Ficanha, Houghton, MA (US); Kenton Kaufman, Rochester, MN (US)

(73) Assignees: Mayo Foundation For Medical Education And Research, Rochester, MN (US); Michigan Technological University, Houghton, MI (US)

( * ) Notice: Subject to any disclaimer, the term of this patent is extended or adjusted under 35 U.S.C. 154(b) by 144 days.

(21) Appl. No.: 14/663,130

(22) Filed: Mar. 19, 2015

(65) Prior Publication Data
US 2015/0265425 A1 Sep. 24, 2015

Related U.S. Application Data

(60) Provisional application No. 61/955,470, filed on Mar. 19, 2014.

(51) Int. Cl.
*A61F 2/66* (2006.01)
*A61F 2/68* (2006.01)
(Continued)

(52) U.S. Cl.
CPC .............. *A61F 2/6607* (2013.01); *A61F 2/66* (2013.01); *A61F 2/68* (2013.01); *A61F 2/76* (2013.01); *A61F 2/80* (2013.01); *A61F 2002/5093* (2013.01); *A61F 2002/607* (2013.01); *A61F 2002/6664* (2013.01); *A61F 2002/701* (2013.01); *A61F 2002/704* (2013.01); *A61F 2002/7645* (2013.01); *A61F 2220/0091* (2013.01)

(58) Field of Classification Search
CPC ............. A61F 2/60; A61F 2/66; A61F 2/6607
See application file for complete search history.

(56) References Cited

U.S. PATENT DOCUMENTS 315,519 A * 4/1885 Lockwood ............ A61F 2/6607
623/49
959,881 A * 5/1910 Price ......................... A61F 2/64
623/33

(Continued)

*Primary Examiner* — Marcia Watkins
(74) *Attorney, Agent, or Firm* — Quarles & Brady LLP

(57) ABSTRACT

A system and method for operating a prosthesis is provided. The system includes a socket configured to engage a residual limb of a subject and a shaft having a first end connected to the socket and an opposing second end. The system also includes a foot piece connected to the second end of the shaft. The foot piece includes an ankle plate and a sole piece configured to contact a surface. The system also includes at least one computer configured to detect a state of the foot piece and to transmit an indication of the state of the foot. The system further includes a motor assembly configured to receive the indication of the state of the foot and to control a position and impedance of the ankle plate based on the state of the foot.

21 Claims, 19 Drawing Sheets

(51) Int. Cl.
  *A61F 2/80*  (2006.01)
  *A61F 2/76*  (2006.01)
  *A61F 2/60*  (2006.01)
  *A61F 2/70*  (2006.01)
  *A61F 2/50*  (2006.01)

(56) References Cited

U.S. PATENT DOCUMENTS

2010/0113980 A1* 5/2010 Herr .......................... A61F 2/60
                                                            600/587
2010/0241242 A1* 9/2010 Herr .......................... A61F 2/60
                                                            623/24
2011/0009982 A1* 1/2011 King .................... A43B 7/1425
                                                            623/53

\* cited by examiner

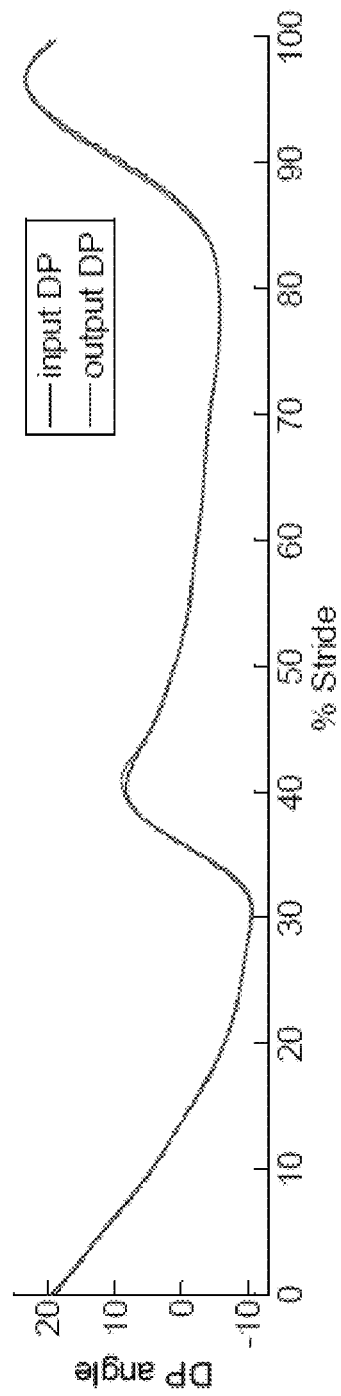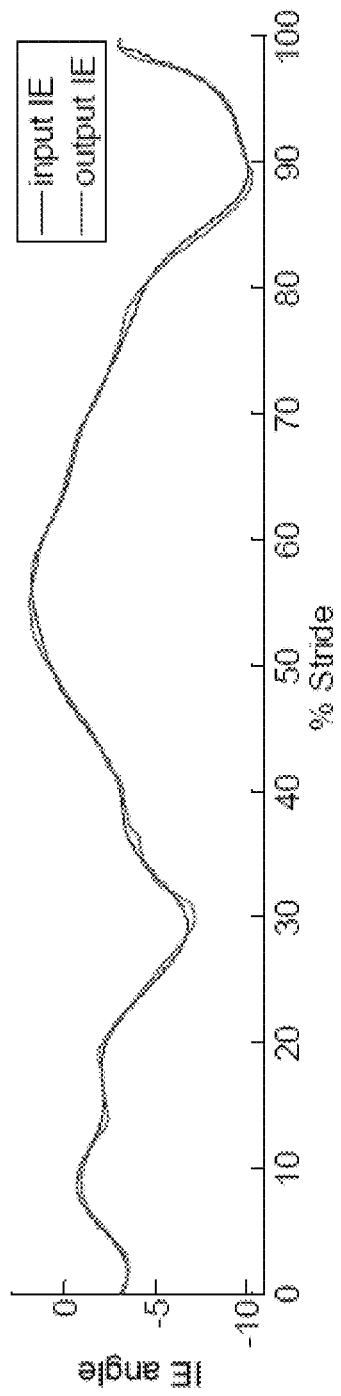

SYSTEM FOR POWERED ANKLE-FOOT PROSTHESIS WITH ACTIVE CONTROL OF DORSIFLEXION-PLANTARFLEXION AND INVERSION-EVERSION

CROSS-REFERENCE TO RELATED APPLICATIONS

This application is based on, claims the benefit of, and incorporates herein by reference, U.S. Provisional patent application Ser. No. 61/955,470, filed on Mar. 19, 2014, and entitled "Powered Steerable Ankle-Foot Prosthesis".

STATEMENT REGARDING FEDERALLY SPONSORED RESEARCH

This invention was made with government support under CBET-1350154-01 awarded by the National Science Foundation. The government has certain rights in this invention.

BACKGROUND

The present disclosure is directed to systems and methods of making and using prosthesis. More particularly, the present disclosure relates to systems and methods of making and using multi-axial powered ankle-foot prosthesis.

Walking in a straight line requires complex modulation of a person's muscle contractions to control the stiffness of the person's ankle and to generate forward propulsion. Similar muscle contractions are required to generate the appropriate ground reaction forces to steer the body while turning.

People having amputations below the knee who use passive prosthesis have been found to expend 20-30% more energy than non-amputees to walk at an equivalent speed. The increase in energy expenditure results in a preferred walking speed which is 30-40% slower than non-amputees. Powered prostheses have been developed to reduce the metabolic cost during straight walk by providing energy to the gait at push-off.

Ankle-foot prostheses provide locomotion assistance to amputees, emulating the function of the healthy ankle. Quasi-static impedance (stiffness) and mechanical impedance of the ankle in the sagittal plane have been used in the design of ankle-foot prostheses to allow for the production of positive work during gait. Conventional, commercially available, prosthetics have been designed to actively control one degree of freedom in the sagittal plane. For example, some have developed a knee and ankle prosthesis capable of controlling the impedance of both the knee and ankle joints in the sagittal plane by controlling the neutral position of the foot during gait. Systems available from BiOM provide the energy during plantarflexion, actively contributing in gait and lowering metabolic cost. The controller in BiOM systems allow for gait in different cadence over surfaces with different inclinations. The Proprio Foot from Ossur uses a stepper motor to provide dorsiflexion motion during swing forward, as well as adjustment of the ankle angle on the surface with different terrains. A controller used with Ossur uses a pattern recognition algorithm to continuously adapt to the user's gait. As another example, Elan from Endolite uses a hydraulic ankle, and the controller provides for foot clearance and plantarflexion for support during stance by adjusting the ankle joint resistance. While the aforementioned prostheses improve the gait of amputees, they are designed to modulate the ankle torques in the sagittal plane only.

In addition, the focus of powered prosthesis has been on increased mobility in forward locomotion. However, studies show that in average, 25 percent of an average person's steps have been found to be turning steps. Two different strategies are commonly used for turning. Spin turn requires the person to turn the body around the leading leg. For example, the person may turn right with right leg in front. Step-turn requires the person to shift their body weight to the leading leg while simultaneously stepping the opposite leg in. The step-turn has shown to allow for increased stability when turning.

It has been shown that the velocity, length, and width of a step-turn are considerably different than the straight walk. Additionally, turning requires modulation of the ankles impedance in both Dorsiflexion-Platarflexion (DP) and Inversion-Eversion (IE) planes to control the lateral and forward reaction forces to maintain the person's center of mass along the desired trajectory. Therefore, the ground reaction forces exhibited during a step-turn are greater than those experienced during a straight walk.

Due to the lack of appropriate propulsion provided by passive prostheses, amputees rely on different gait strategies than non-amputees. Non-amputees have been found to rely mainly on their ankle rotation in the sagittal plane and hip rotations in the coronal plane when turning. Conversely, amputees rely on their hip rotations in both the sagittal plane and the coronal plane when turning. Consequently, energy consumption during each step is significantly higher for an individual with a conventional transtibial prosthetic. The energy consumption required at each step in an average able-bodied human weight 70 kg is between 36 J/step for walking and up to 100 J/step for running. Energy consumption for an individual having a conventional prosthetic may increase by as much as 35%.

When physical systems interact with each other, they behave either as an impedance or an admittance. A system that behaves as an impedance accepts external motion inputs and generates force outputs. Systems that behave as an admittance accept external force inputs and generate motion outputs. Coupled mechanical systems must physically complement each other, meaning that in any degree of freedom, if one system is an admittance, the opposing system must be an impedance.

During gait, at the moment the heel interacts with the ground, also referred to as "heel-strike", the ankle accepts the external force and generates the appropriate motion, so it may be considered a system in admittance. Conversely, at push-off the ankle generates the necessary torques to produce a desired motion, and may therefore be considered as a system an impedance.

Therefore, further development of prosthesis is needed to provide amputees with more efficient and effective movements that more accurately approximate the function of natural limbs.

SUMMARY

The present disclosure provides systems and methods for powered prosthesis capable of providing power in both DP and IE. Furthermore, the present disclosure provides a prosthesis that can utilize impedance modulation at push-off and admittance modulation at heel-strike to provide for maneuverability and stability correlated with that of a healthy human ankle.

In accordance with one aspect of the disclosure, a prosthesis is provided that includes a socket configured to engage a residual limb of a subject and a shaft having a first end connected to the socket and an opposing second end. The prosthesis also includes a foot piece connected to the second end of the shaft, the foot piece comprising an ankle plate and a sole piece configured to contact a surface. The prosthesis also includes at least one computer configured to detect a state of the foot piece and to transmit an indication of the state of the foot and to a motor assembly configured to receive the indication of the state of the foot and to control the impedance and the position of the ankle plate based on the state of the foot.

In accordance with another aspect of the disclosure, a method of actuating a prosthesis is provided that includes sensing a state of the prosthesis, transmitting the state of the prosthesis to a computer, determining a desired trajectory and impedance for the prosthesis, generating a desired motion and impedance using a motor assembly to propel the prosthesis through the desired trajectory, and anticipating a future trajectory and impedance of the prosthesis using a vision sensor.

The foregoing and other advantages of the invention will appear from the following description.

BRIEF DESCRIPTION OF THE DRAWINGS

FIG. 16A is a graphical representation of an ankle trajectory output in the DP direction that closely follows an input reference of human ankle rotations during a step turn and the prior swing period.

FIG. 16B is a graphical representation of an ankle trajectory output in the IE direction that closely follows an input reference of human ankle rotations during a step turn and the prior swing period.

DETAILED DESCRIPTION OF THE PREFERRED EMBODIMENT

Figure 1:
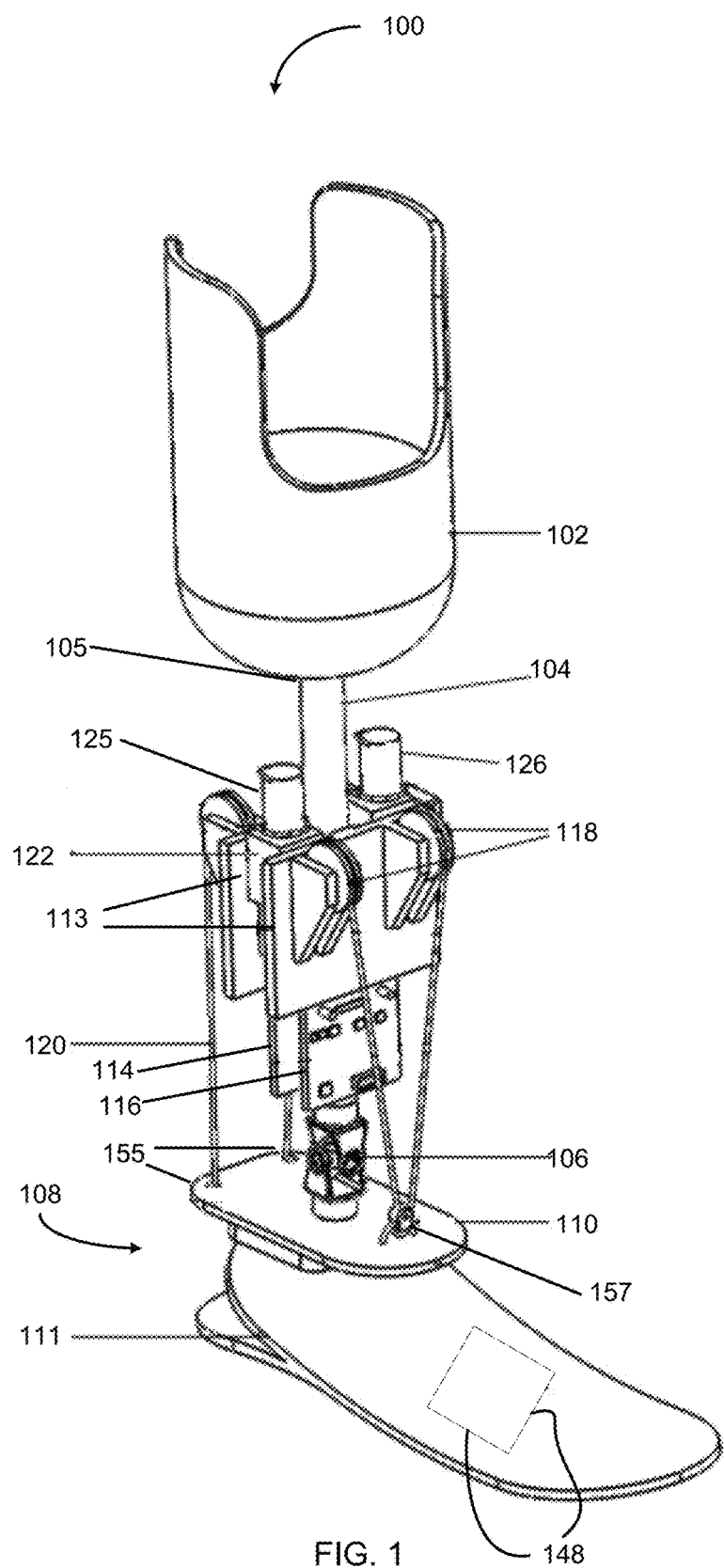
FIG. 1 is a representation of a prosthesis according to the present disclosure.
Figure 2:
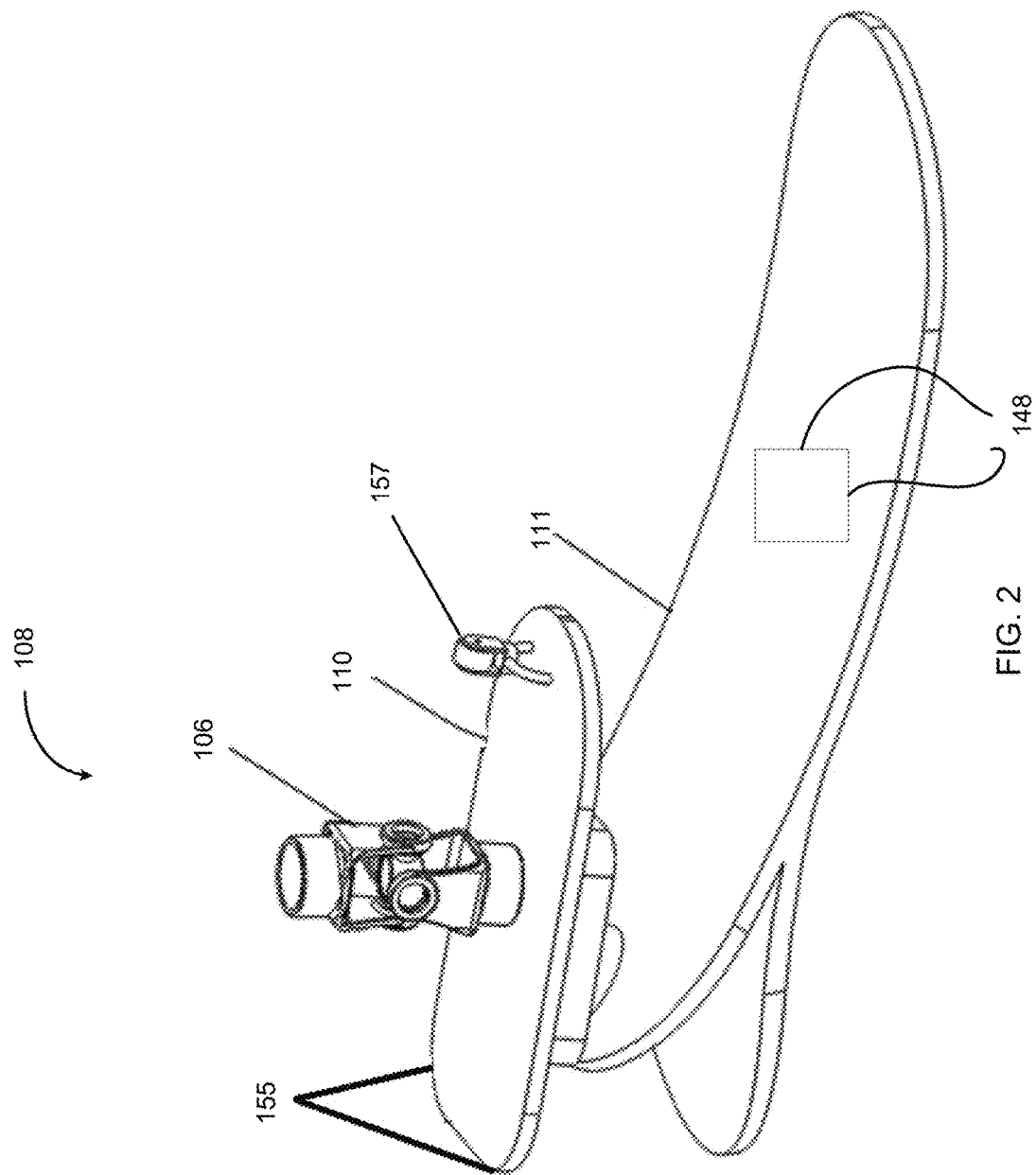
FIG. 2 is a representation of a foot piece of a prosthesis according to the present disclosure.

Referring to FIG. 1, a prosthesis 100 is presented. It is possible for the prosthesis 100 to be a steerable, transtibial prosthesis. The prosthesis 100 includes a socket 102 configured to engage a residual limb of a subject (not shown), a shaft 104 having a proximal end 105 connected to the socket 102 and a distal end connected to a foot piece 108. The foot piece 108 includes an ankle plate 110, for example a carbon-fiber or fiberglass-composite material plate with specific stiffness designed for the user's weight, and a sole piece 111. The foot piece 108 can also be seen in FIG. 2.

The ankle plate 110 may be configured to provide a multi-axis ankle having at least two degrees-of-freedom (DOF), which can enhance gait efficiency by extending the control of IE and DP during walking in both a straight line and turning. The ankle plate 110 can be designed to transfer the force from a cable 120 to the sole piece 111, and may act as a spring connected in series with the cable. The multi-axis ankle can allow the prosthesis 100 to adapt to uneven and inclined ground surfaces.

The foot piece may also include a joint 106 which can be designed to support the subject's weight and apply rotational torque in the transverse plane from the ground to the user with no constraint in the DP and IE direction. It is possible for the joint 106 to be surrounded by an elastomer to provide passive stiffness and damping to the ankle plate 110 in DP and IE directions.

The prosthesis 100 may further include a set of parallel plates 113 configured to connect the shaft 104 to a motor assembly 112. The motor assembly 112 may include a first motor 128, a second motor 130, a first gearbox 122, a second gearbox 124, a first cable drum 125, and a second cable drum 126, a plurality of pulleys 118 and at least one cable 120 which will be discussed in greater detail below.

Figure 3:
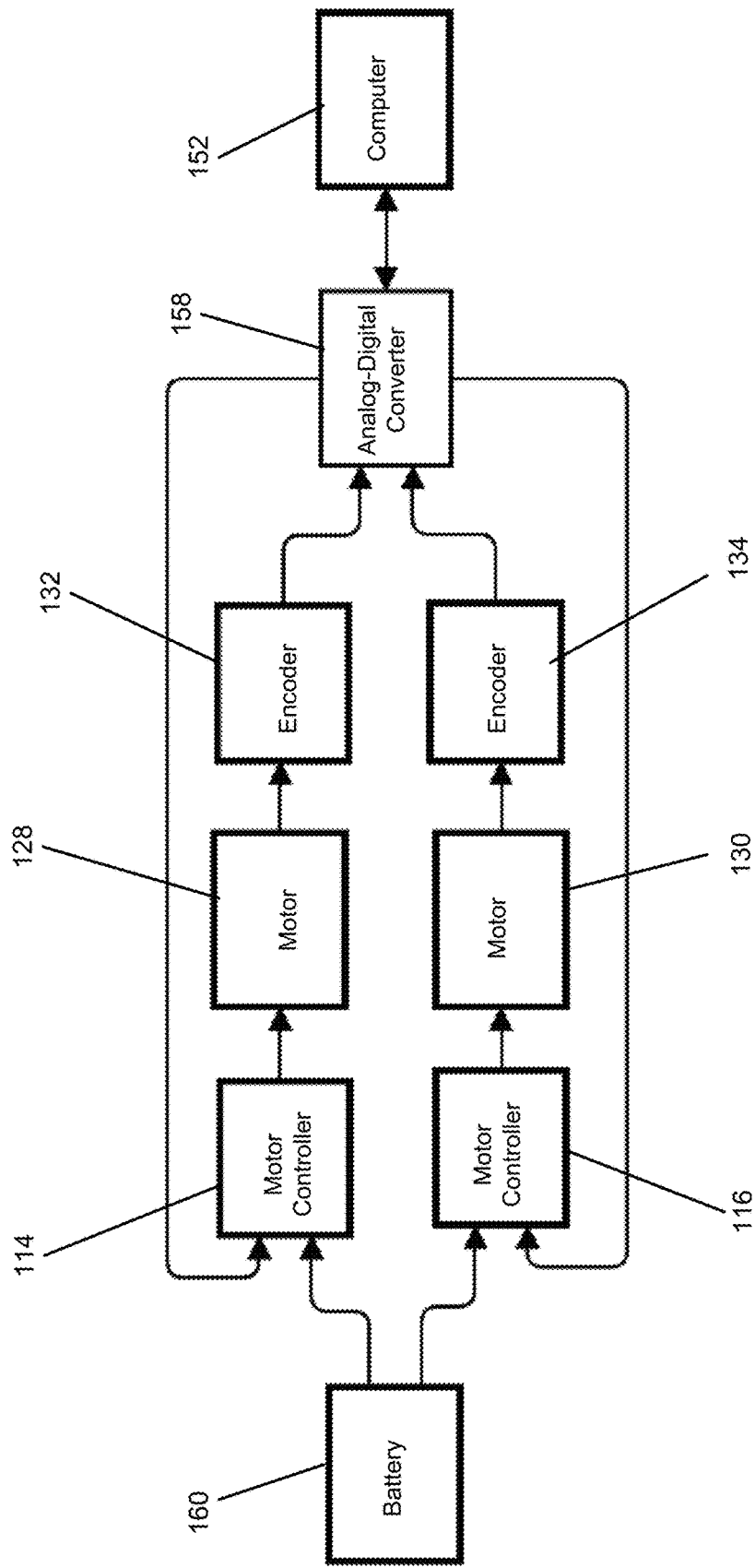
FIG. 3 is a schematic of a set of elements configured to control a prosthesis according to the present disclosure.

As seen in FIG. 3, the prosthesis 100 may also include a first motor controller 114 and a second motor controller 116 configured to receive power from a battery 160 and to provide power to the first and second motors 128,130. The first and second motors 128, 130 may be configured to send signals to a first quadrature encoder 132 and to a second quadrature encoder 134 connected to a computer 152.

Figure 4A:
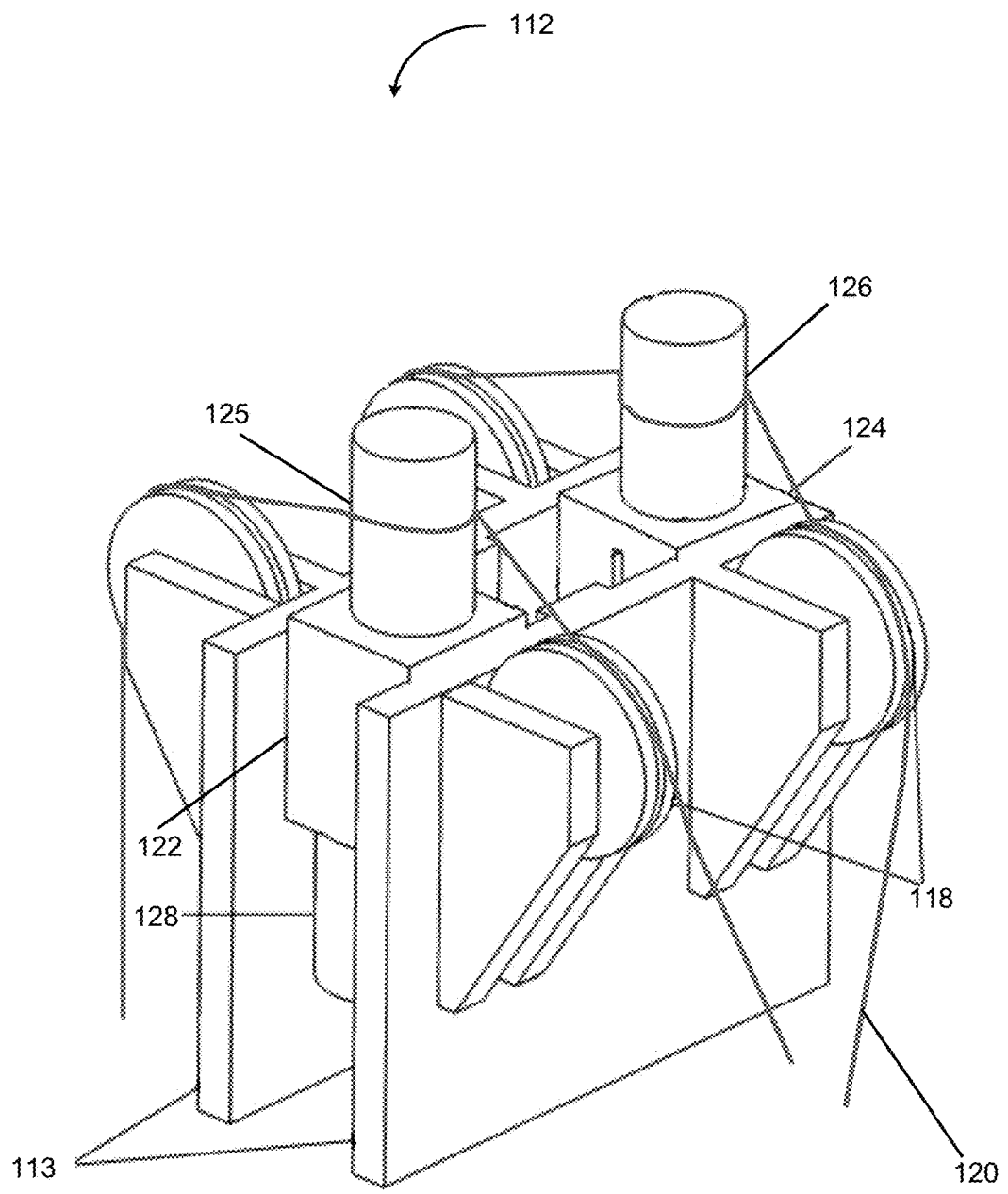
FIG. 4A is a representation of a motor assembly of a prosthesis.
Figure 5:
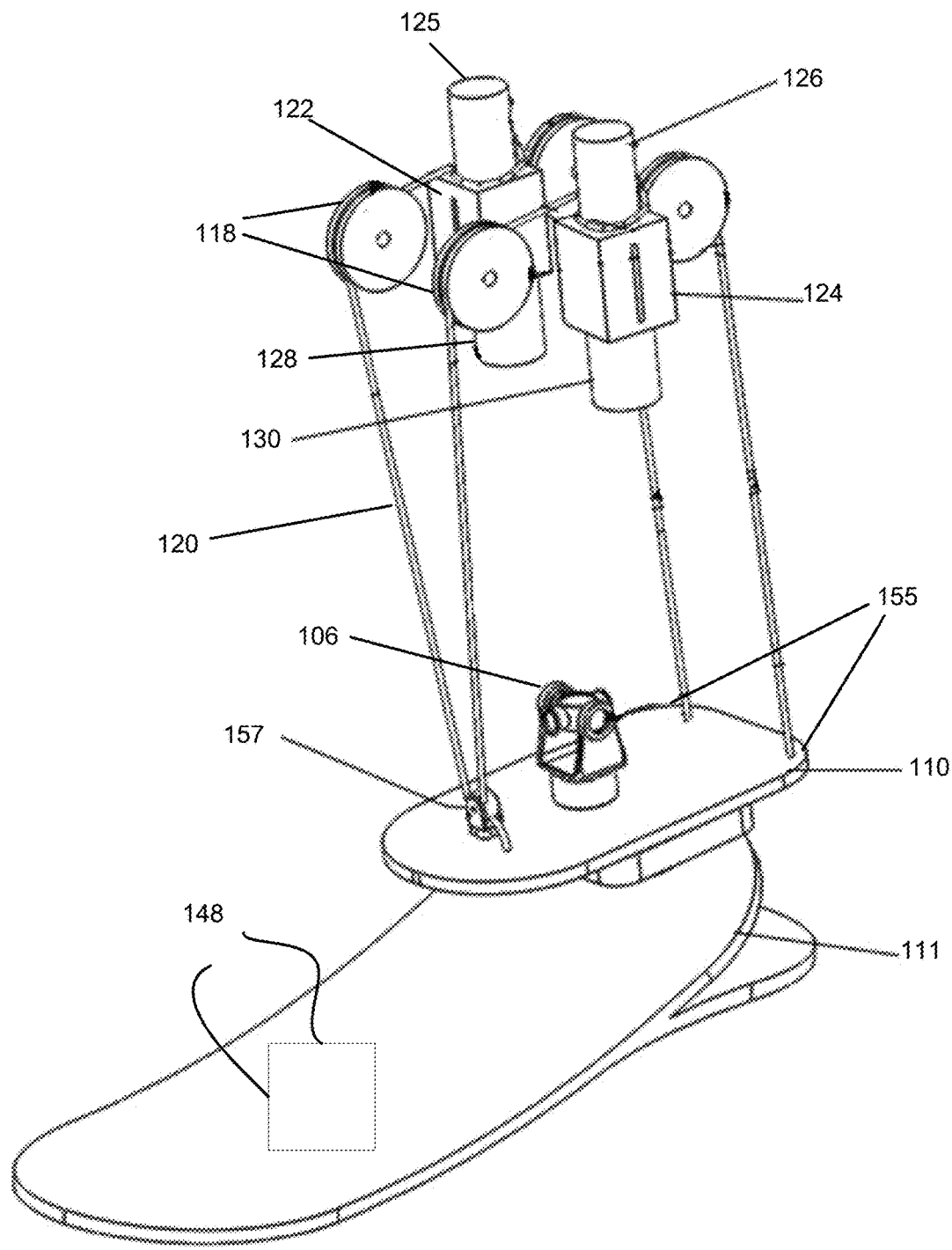
FIG. 5 is a representation of a portion of a prosthesis including the foot piece, the motor assembly, and a cable.

The motor assembly 112 can be seen in FIG. 4A and FIG. 5. Disposed between the set of parallel plates 113 are the first gear box 122 and the second gear box 124. The first cable drum 125 may be fixed to a proximal end of the first gear box 122, and the second cable drum 126 may be fixed to a proximal end of the second gear box 124. Additionally, the first motor 128 may be attached to a distal end of the first gear box 122, and the second motor 130 may be attached to a distal end of the second gear box 124.

In one example, the at least one cable 120 runs from a rear corner 155 to the first cable drum 125, to a pulley 157 in front of the ankle plate 110, back to the second cable drum 126, and back to the second rear corner 155. The cable 120 is rigidly attached to the first and second cable drums 125, 126 to avoid slipping. It is possible for the cable 120 to be attached near a central axis of the first and second cable drums 125,126. It is also possible for the cable 120 to be securely attached to the first and second cable drums 125, 126 with a fastener, for example a screw.

Activation of the at least one cable 120 may allow for DP when the motors rotate in opposite directions, and for IE when the motors rotate in the same direction. Varying combinations of DP and IE can be obtained by combining different amounts of rotation in each motor. It is also possible for the first motor controller 114 and second motor controller 116 to be programmed to allow for alternative rotation combinations to provide for DP and IE.

Figure 4B:
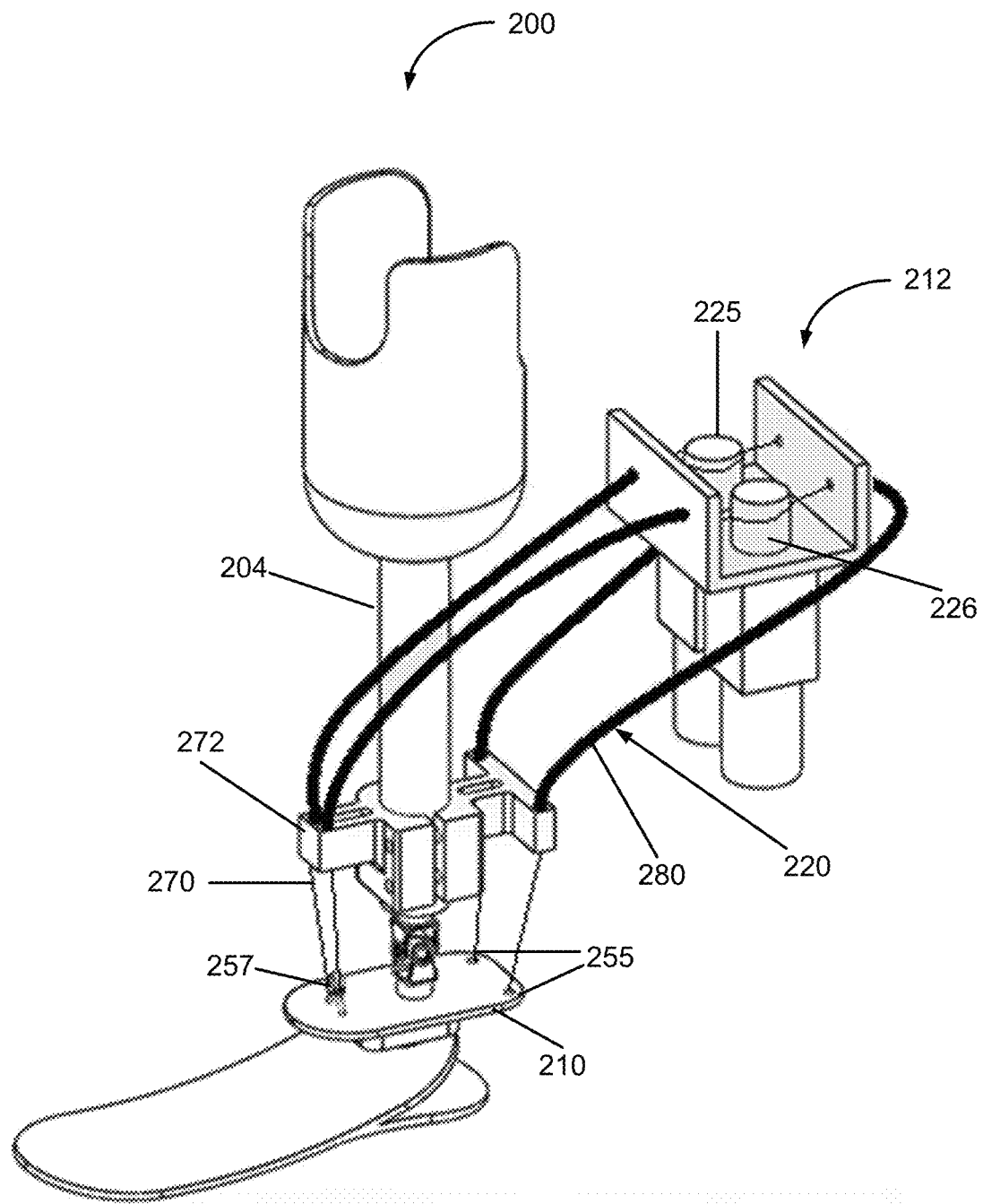
FIG. 4B is a representation of a prosthesis according to the present disclosure.

In an additional configuration of the prosthesis 200, having similar reference numerals to the aforementioned configuration, as shown in FIG. 4B, the at least one cable 220 of the motor assembly 212 is a Bowden cable 220. In one example, an inner cable 270 of the Bowden cable 220 is configured to transfer a force to the ankle plate 210. The inner cable may pass through four outer housings 280, two of which providing a path from the motor assembly 212 to the pulley 257 in front of the ankle plate 210, and the additional two outer housings 287 providing a path from the motor assembly 212 to the two rear corners 255 of the ankle plate 210.

The Bowden cable 220 may be connected to a bracket 272 movably connected to the shaft 204 rather than the plurality of pulleys 118, and further connected to the first and second cable drums 225, 226. The Bowden cable 220 may be permanently in tension, and a torque may be transferred from the first and second cable drums 225, 226 through the Bowden cable 220, to the ankle plate 210. Thus the plurality of pulleys 118 may be removed from the motor assembly 212. It is possible for the motor assembly 212 to be placed in a location alternative to the shaft. It is also possible for the motor assembly 212, the first and second motor controllers 214, 216, the battery 260, and the computer 252 to be removed from the prosthesis 200, such that the prosthesis 200 behaves as a passive prosthesis.

It is possible for the computer 152 to administer an impedance controller to the first motor controller 114 and the second motor controller 116, which can accept external motion inputs and generate output torques. The impedance controller may receive position feedback and torque feedback as detailed below.

The impedance controller can use position encoders mounted within the first gear box 122 and the second gear box 124 to determine a position of the foot. A plurality of torque sensors 148, for example strain gauges, integral with the foot piece 110 may be used to estimate a ground reaction torque feedback. The desired position and the determined position may be used to derive an input to the first motor 128 and the second motor 130 using an impedance control. The torque feedback, together with the desired torque may be used to derive an input to the first motor 128 and the second motor 130 using an impedance control. It should be noted that the reference angle for the first motor controller 114 is the sum of the DP and IE angles, while the reference angle for the second motor controller 116 is the difference between the DP and IE angles.

It is possible for the computer 152 to administer an admittance controller, which can accept external torque inputs and generate output motions. The admittance controller may use ground reaction torque feedback to estimate the appropriate actuator position. The desired actuator's position and position feedback can be used to estimate the appropriate actuators inputs.

Similar to the impedance controller, the torque feedback for the admittance controller may be the sum of the DP and IE ground reaction torques, while the feedback torque for the second motor controller 116 may be the difference between DP and IE environment torques.

The admittance controller can use a look-up data table to update an inner position control. The inner-position control can integrate the ground reaction torque feedback in DP to increase the index of the look-up table of the ankle angles proportionally to the external torque. Therefore, an external torque input can allow for the prosthesis 100 to follow a pre-recorded angular trajectory while admitting external torque to produce motion. An absence of an external torque will keep the prosthesis 100 stationary.

At heel-strike, the prosthesis 100 does not move unless it contacts the ground. Therefore, the prosthesis 100 can move automatically based on the external torque feedback. It can be noted that the admittance controller may engage when the motion of the device is known, and the external torque may be used to control the velocity of the trajectory of the prosthesis 100.

It is also possible for the computer 152 to administer an admittance controller or an impedance controller. The motor assembly 120 may further include a plurality of pulleys 118 joined to the ankle plate 110 and configured to provide a track for the at least one cable 120. First and second cable drums 125, 126 can be configured to transfer a torque to the connecting plate 110 through the cable 120. The cable 120 may be connected to the connecting plate 110 at a plurality of locations. In one example, the cable 120 is integral with the two rear corners 155 of the ankle plate 110, and runs through a pulley 157 connected to the front of the plate. The pulley 157 can allow for DP and IE torque to be decoupled.

A finite-state machine 156 maybe be configured to select between impedance and admittance control in both DP and IE. The finite-state machine 156 receives external torque values in both DP and IE, the external torque values being measured by the plurality of torque sensors 148 integrated within the foot piece 110. In one example, the finite-state machine 156 can be connected to the computer 152, and may be configured to acquire pre-recorded data and to provide motor controller inputs.

Figure 6:
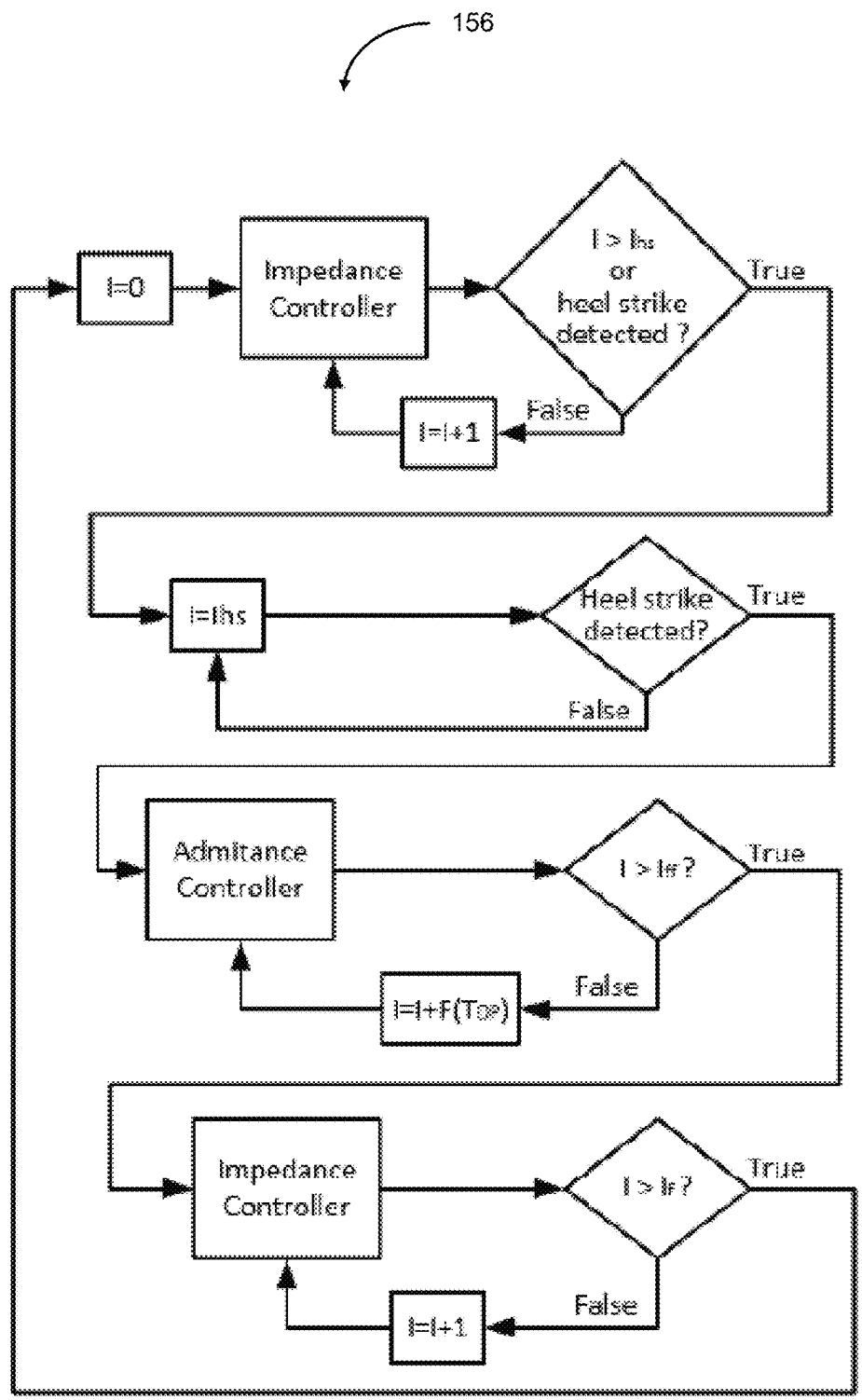
FIG. 6 is a process flow chart for a set of controllers configured to maneuver a prosthesis.

One example process flow of the finite-state machine 156 can be seen in FIG. 6. The process may start at the middle of the swing phase and move with the active impedance controller to the expected heel-strike orientation. If heel-strike by the finite-state machine 156 is detected before it is expected (e.g. the user starts to walk faster), the finite-state machine skips the rest of the swing phase and starts the heel-strike phase immediately with the admittance control.

If the finite-state machine 156 does not detect a heel-strike (e.g. the user starts to walk at a slower speed), the prosthesis can advance to the angle at the beginning of the heel-strike phase and can hold the position until heel-strike is detected. When the prosthesis reaches foot-flat, the control switches back to an impedance controller until the foot reaches the middle of the swing phase, where the process resets to zero and the cycle begins again.

EXAMPLES

The following Examples are provided in order to demonstrate and further illustrate certain embodiments and aspects of the present disclosure and are not to be construed as limiting the scope of the disclosure.

Example 1—Determination of Ankle Range-of-Motion

Human Subjects

Five male subjects with no self-reported neuromuscular and biomechanical disorders were analyzed. The subjects were ages 23 to 26 years and had a body mass index from 18.5 to 27.5.

Experimental Setup

A motion capture camera system was used to track the rotations of the foot and tibia of the subjects. The system consisted of 8 cameras covering a perimeter of a testing area, with 4 cameras disposed in the corners and 4 additional cameras disposed between the corners, the cameras covering 16 cubic meters and 12 cubic meters, respectively.

The cameras emitted infrared light and captured the reflected light from reflectors mounted on the subjects with a rate of 250 Hz. Three reflectors were sufficient for the camera system to calculate the position and orientation of a rigid body at any time if each reflector was visible to at least three cameras. Each rigid body had a redundancy of reflectors to avoid the body obstructing the reflectors from being observed by the cameras.

The subjects wore a shoe and a knee brace mounted with five reflector markers each. The shoe and the knee brace assured that the reflectors would not move with respect to each other.

Experiment

To establish a local coordinate system, the subjects were asked to stand still in the center of the testing area, facing the direction that they would be walking. The global coordinate system was defined such that the subject walked in the direction of the positive Y-axis and turned left in the negative x-axis direction. The global coordinate system needed to be defined for each subject. After recording the trajectories of the markers, the markers that were mounted on each object, for example a shoe or a knee brace, were defined as a unitary object and a local coordinate system was defined at the geometric center of the markers. The local coordinate system had the same orientation as the global coordinate system. A right-handed global Cartesian coordinate system was also established for the testing area.

In addition, the angles of the foot with respect to the leg were characterized. The position and orientation of the leg and the foot were determined relative to the global coordinate system. In addition, the position and orientation of the foot relative to the leg was determined.

To calculate the orientation of the foot and leg at each state of the gait, the global X axis of the foot was used to estimate the heel-strike (consisting of heel-strike and loading response phases), foot-flat (mid-stance phase), and toe-off (terminal stance and pre-swing phases) in each step. It should be noted that the foot angle is positive before heel-strike because the heel is on the ground and the toes are elevated, zero when the foot is flat on the ground, and negative at toe-off when the heel is elevated and the toes are on the ground.

Figure 7A:
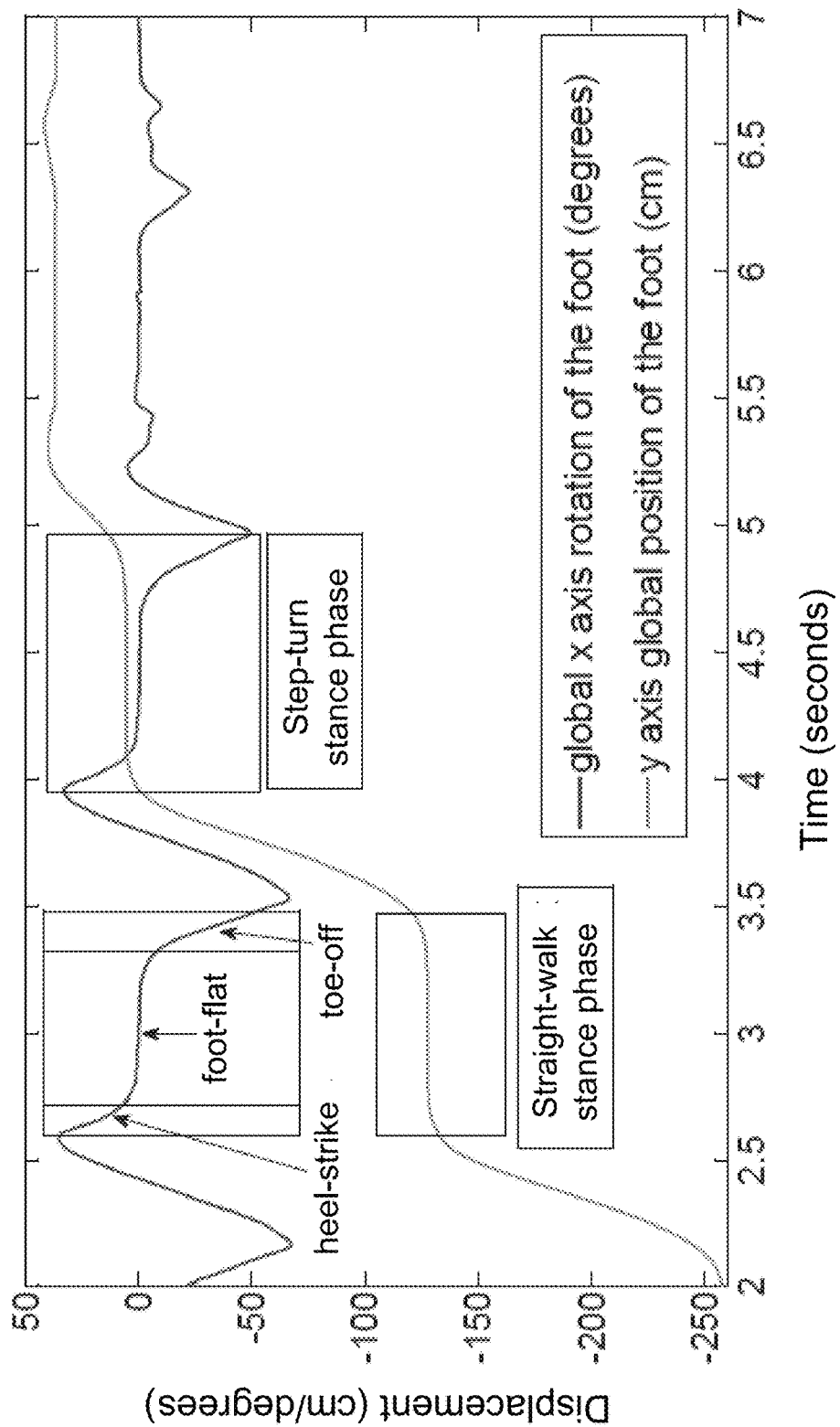
FIG. 7A is a graphical representation of global positioning of the human foot used to determine states of gait.

The global position of the foot in the Y axis was used to estimate if the subject was walking straight or turning, in addition to the start and end of the stance periods. The increased displacement in the Y-direction during the swings of the leg prior to the step-turn that remained near constant afterwards was used as an indicator of a turn. FIG. 7 shows a plot of the global X axis rotation and Y axis global position of the foot used to identify the points in time where the different states of the gait occurred.

The subjects were instructed to walk at a normal pace and an audible metronome was synchronized to provide for a constant walking speed. The preferred speed for the participants ranged from 88 to 96 steps per minute. The subjects were instructed to walk from outside the field of view of the cameras while following a straight, marked path on the floor. A reference point on the floor was placed to identify a location for the subject to turn. The subject performed a 90° step-turn to the left, pivoting on their right leg. After the turn, the subject walked straight until they were outside of the field of view of the cameras.

Figure 7B:
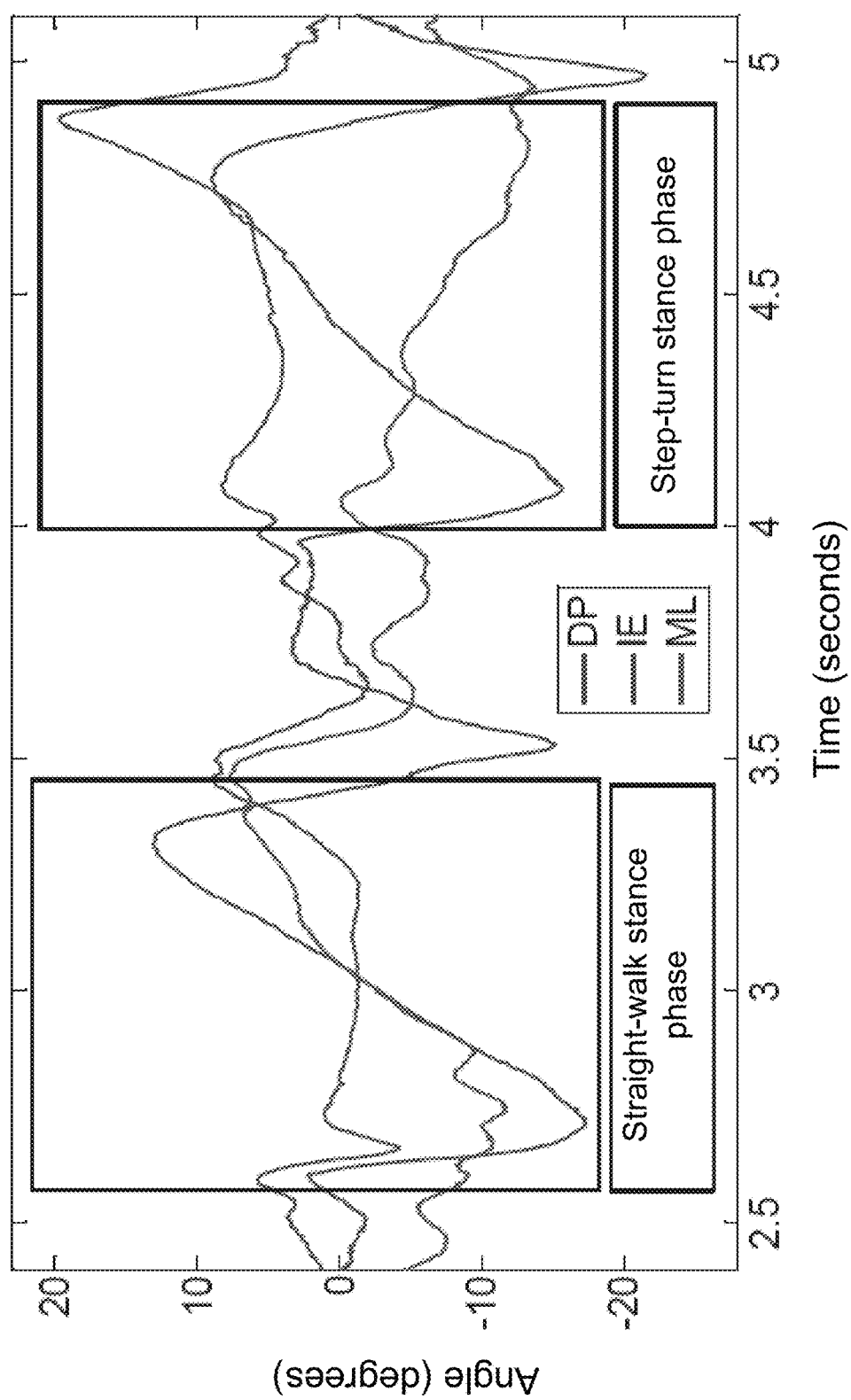
FIG. 7B is a graphical representation of DP, IE, and ML rotations of a human ankle during straight-walk and step-turn.

Plots of DP, IE, and ML of a representative subject can be seen in FIG. 7B. The data of each test was divided into 6 segments; heel-strike, foot-flat, and toe-off during both straight step and step-turn. The averages of the DP, IE, and ML angles of each segment were calculated for each of the 45 tests (9 tests on 5 subjects). Table 1 below shows the average ROM for the straight step and step-turn during the stance periods.

TABLE 1

| | ROM of Straight Step Stance Period (deg) | | ROM of Step-turn Stance Period (deg) | | |
|---|---|---|---|---|---|
| | Degrees | Standard Error | Degrees | Standard Error | % Change |
| DP | 33.9 | 0.65 | 31.6 | 0.62 | −7.4 |
| IE | 15.69 | 0.52 | 20.6 | 1.06 | 23.8 |
| ML | 22.09 | 0.6 | 16.8 | 0.65 | −31.9 |

Table 2 below shows the average rotations and the difference in angles from the turning step to the straight step in each phase. The range of motion about the three axes and average rotations were calculated for each subject's ankle in each state of the walk. Each subject's range of motion was used to calculate the average percent change from straight walk to step-turn with respect to the individual's ROM in straight step.

TABLE 2

| | Straight Step Average (deg) | Standard Error | Turning Step Average (deg) | Standard Error | Angular Change (deg) | % Change |
|---|---|---|---|---|---|---|
| DP heel-strike | −8.72 | 0.80 | −9.68 | 0.95 | −0.95 | −3.00 |
| DP foot-flat | 2.34 | 0.63 | 0.36 | 0.64 | −1.98 | −6.50 |
| DP toe-off | 10.59 | 1.24 | 1.37 | 0.90 | −9.22 | −29.20 |
| IE heel-strike | −1.72 | 0.53 | 5.90 | 0.63 | 7.61 | 46.60 |
| IE foot-flat | −2.93 | 0.27 | 6.51 | 0.22 | 9.44 | 60.50 |

TABLE 2-continued

| | Straight Step Average (deg) | Standard Error | Turning Step Average (deg) | Standard Error | Angular Change (deg) | % Change |
|---|---|---|---|---|---|---|
| IE toe-off | 1.44 | 0.45 | 13.61 | 0.46 | 12.17 | 82.00 |
| ML heel-strike | −5.34 | 0.57 | 0.34 | 0.62 | 5.68 | 25.60 |
| ML foot-flat | −0.90 | 0.45 | −3.55 | 0.41 | −2.65 | −12.80 |
| ML toe-off | 5.53 | 0.32 | −6.53 | 0.65 | −12.06 | −58.00 |

Discussion

A modest decrease in DP ROM during the step-turn compared to the straight step can be seen in Table 1. IE ROM increased by 23.8%, indicating an increase in IE activity during steering. A significantly smaller ML ROM suggested a higher stiffness in the ML axis of rotation was necessary to transfer the reaction forces from the ground to the body.

As the step progressed through the gait, differences in the ROM were observed between the straight step and step-turn for all subjects. During step-turn, the initial angle of −9.68° of dorsiflexion in the DP axis was similar to that of straight step. However, at toe-off the angle of plantarflexion was found to be 1.37° during step-turn as compared to 10.37° during straight walk, indicating less forward propulsion during step-turn.

During step-turn IE started with 5.9 degrees of inversion, and gradually increased to 13.6° at toe-off indicating a gradual increase in inversion to lean the body toward the inside of the turn. At heel-strike ML had 5.6 degrees of medial rotation indicating an anticipatory motion of the foot, and transitioning to 12 degrees of lateral rotation at toe-off generated by pivoting the body on top of the foot.

Example 2—Motor Assembly

In one example, two brushed DC motors and motor controllers capable of a continuous torque output of 0.25 N/m at 9200 RPM (240 Watts each) were used to provide the work needed for propulsion. An 11.1 Volts and 5 AH LiPo battery with an energy density of 159 Wh/kg was used to provide energy for an estimated 2400 steps. A planetary gear reduction with a 104:1 ration was used to increase torque, and to deliver the necessary torque during locomotion. Optical encoders were used to give position feedback to a remote computer.

Example 3—Ankle Torque and Angle Feedback

Test Setup

Figure 8A:
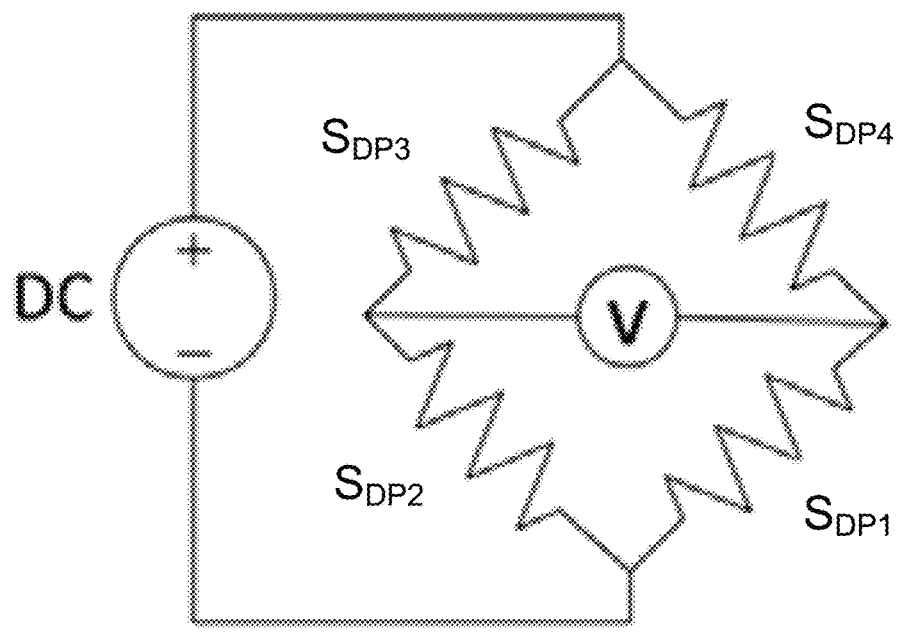
FIG. 8A is a schematic of a Wheatstone Bridge used to determine DP rotation.
Figure 8B:
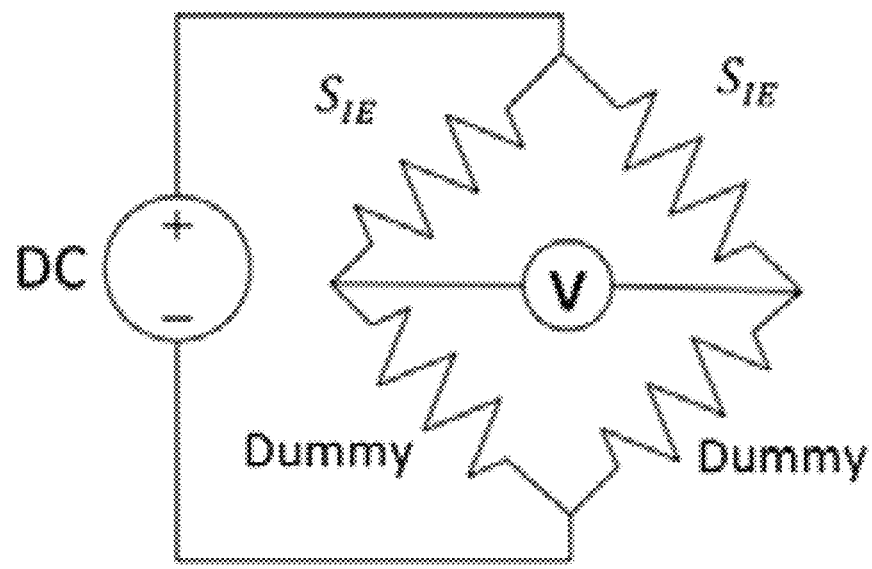
FIG. 8B is a schematic of a Wheatstone Bridge used to determine IE rotation.

A plurality of strain gauges configured in a Wheatstone bridge configuration as shown in FIG. 8A and FIG. 8B were used to estimate torque feedback and to develop a finite-state machine. A decrease or increase in resistance of two of the strain gauges on opposite sides of the Wheatstone bridge caused a decrease or increase, respectively, in the output of the bridge.

Dorsiflexion-Plantarflexion Torque Estimation

To estimate torque in DP, four strain gauges were attached to the sole of a prosthesis prototype. Two strain gauges, $S_{DP1}$ and $S_{DP2}$, as shown in FIG. 8A were located behind the center of rotation of the ankle in DP and were wired into opposite sides of the Wheatstone bridge. Any ground reaction force at the heel caused a decrease in voltage of the Wheatstone Bridge, which can be correlated to the torque in DP of the foot when the heel was interacting with the ground (i.e. heel-strike).

Two strain gauges, $S_{DP3}$ and $S_{DP4}$, as shown in FIG. 8A were located in front of the center of rotation of the ankle in DP, and were wired into opposite sides of the Wheatstone Bridge. Any ground reaction forces from the ground at the front of the foot caused an increase in the output of the Wheatstone Bridge, which can be correlated to the torque in DP of the foot when the forefoot of the foot is contacting the ground (i.e. push-off).

It should be noted that when the foot was flat on the ground, the output from the strain gauges in front of the center of rotation of the ankle cancelled out the output of the strain gauges behind the center of rotation of the ankle. Therefore, the resultant voltage could always be correlated to the net DP torque in the ankle.

Inversion-Eversion Torque Estimation

To estimate torque in IE, two strain gauges were attached to the top of the foot in a Wheatstone Bridge configuration, as shown in FIG. 8B. Two additional dummy gauges were attached to an inert piece of carbon fiber to complete the Wheatstone Bridge. The strain gauges were placed on the outside edge of the foot, and were on the same side of the Wheatstone Bridge. Therefore, the difference in strains of the two strain gauges caused a decrease or increase in the output voltage of the Wheatstone Bridge.

The output voltage could be correlated to the IE torque in the foot when the forefoot of the foot was in contact with the ground (i.e. push-off). This configuration made the Bridge insensitive to torque in DP. Therefore, if both strain gauges contracted or stretched by the same amount as would happen in the presence of a DP torque, the output was not effected.

Correlation of Strain Gauge Readings

The strain gauge readings were correlated to actual disturbance torques using a Kistler® Type 5233A force plate to measure the external force applied during static loading tests. The tests consisted of loading the foot in different configurations, and recording the applied force and the corresponding strain measurement.

Several tests were performed to correlate the strain gauge readings with disturbance torques. These tests consisted of plantarflexion by applying a load when the heel was in contact with the ground, dorsiflexion by applying a load when the forefoot was in contact with the ground, eversion by applying a load when the medial edge of the forefoot was in contact with the ground, and inversion by applying a load when the lateral edge of the forefoot was in contact with the ground.

From the external forces, the geometry of the foot, and the strain measurements, the applied torques were calculated. It should be noted that in DP, the proportional factor between the external force and the strains measured at heel loading and forefoot loading were not the same, because the strain gauges were attached to two different areas of the prosthetic foot.

The proportional factors for the strain gauges at heel loading and forefoot loading were estimated to be 1.41 Nm/volt and 19.52 Nm/volt, respectively in DP. In IE, the proportional factors for inversion and eversion torques were 4.43 Nm/volt and 3.55 Nm/volt, respectively, which was expected because the foot is nearly symmetrical about its sagittal plane.

Example 4—Controller Design

Finite State Machine

Estimated torque feedback from strain gauges in a Wheatstone Bridge configuration and recorded time-history of ankle angles in DP and IE during normal walk were used to develop a finite-state machine to switch between the impedance and admittance controllers.

The recorded ankle angles of an unimpaired human subject were measured using a motion capture camera system. The ankle angles were accessible as a look-up data table to an estate machine and the controllers. The vectors with the ankle data started and finished in the middle of the swing phase (vector indices $I_0$ and $I_f$, respectively). The index for the data at the beginning of the foot-flat (index $I_{ff}$), and expected heel-strike (index $I_{hs}$) were known. These points were used by the finite-state machine to switch from the impedance controller to the admittance controller at heel-strike, and from the admittance controller to the impedance controller at the initiation of a foot-flat phase.

Example 5—Controller Evaluation 1

Impedance Controller Evaluation

To evaluate the impedance controller and its ability to change the quasi-static impedance (stiffness) of the ankle, an experiment was designed to record the quasi-static torque-angle relationship of the prosthesis. The prosthesis was attached to an Anklebot, a lower extremity therapeutic robot. The Anklebot is capable of applying torques and recording angular motion of the ankle in both DP and IE.

Dorsiflexion-Plantarflexion Stiffness

To test the DP stiffness, the prosthesis impedance controller was set at a reference angle of zero degrees and a constant torque feedback gain, K, for each test. Six tests were performed, setting the gain to values ranging from −0.5 to 1.5. In each test, the Anklebot moved the foot from the equilibrium point to 6° dorsiflexion and transitioning to 6° plantarflexion. The movement speed was set to 5°/second, and the data was recorded by the encoders at a sampling rate of 200 samples/second. The results were filtered with a 0.5 Hz cutoff frequency to remove sensor noise.

Figure 9:
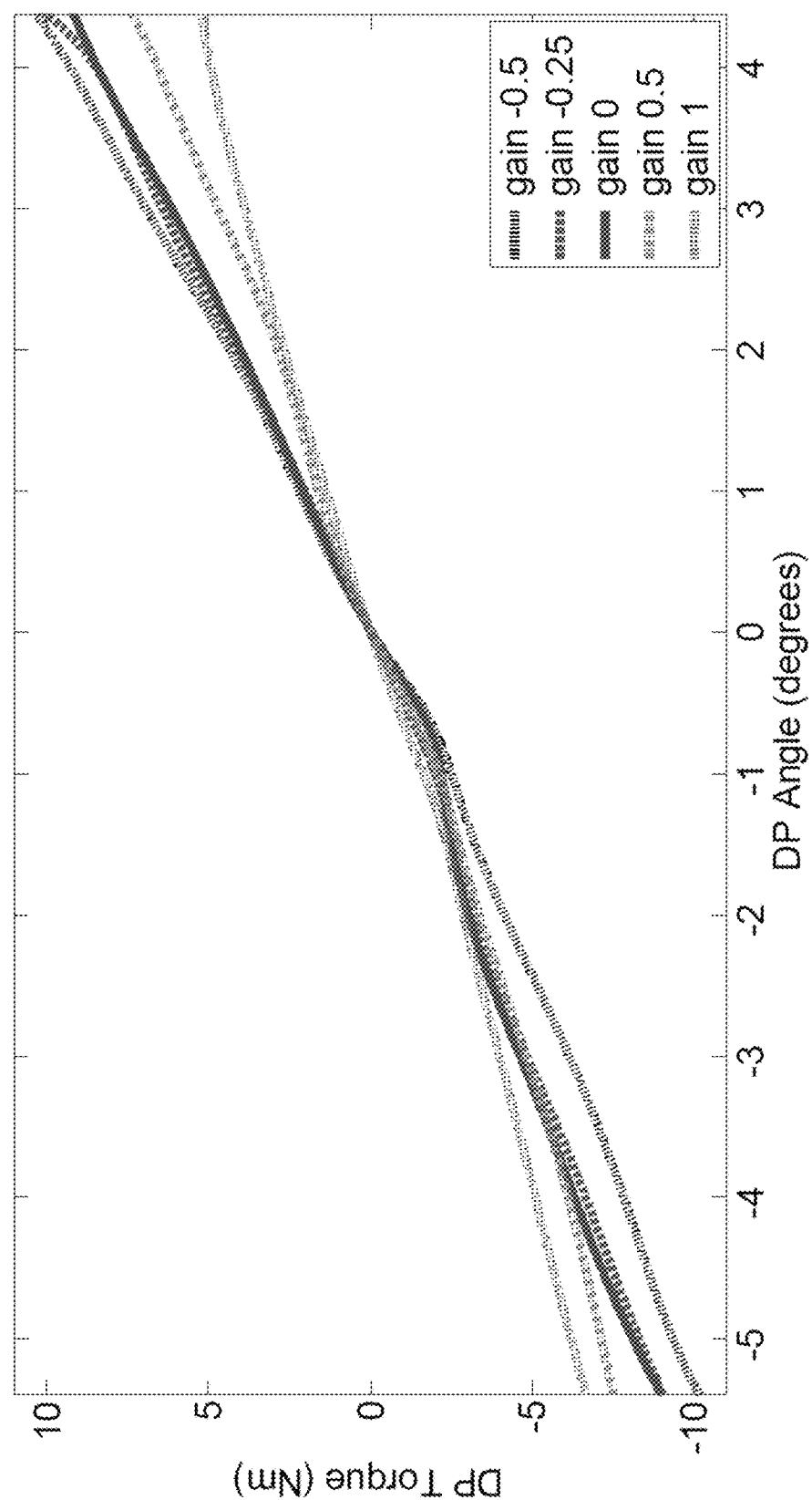
FIG. 9 is a graphical representation of DP angle and torque at different feedback gains sensed according to the present disclosure.

The results of the tests, with varying gains, are shown in FIG. 9, depicting the unloading, transition, and loading phases of the ankle. It can be seen that the change in the feedback gain, correlating to the slope of the torque-angle curve, effectively changed the stiffness of the ankle in DP.

Zero gain caused the prosthesis to behave as a passive prosthesis, as it is not a backdrivable mechanism. Negative gains caused the prosthesis stiffness to increase compared to the zero gain test. Positive gains resulted in a decrease in the prosthesis stiffness when compared to zero gain. All gains produced a near linear change in DP torque with respect to the change in angle, with some deviation near the origin caused by the transition in the ankle from loading to unloading and its effects on the bending of the composite plate.

Figure 10:
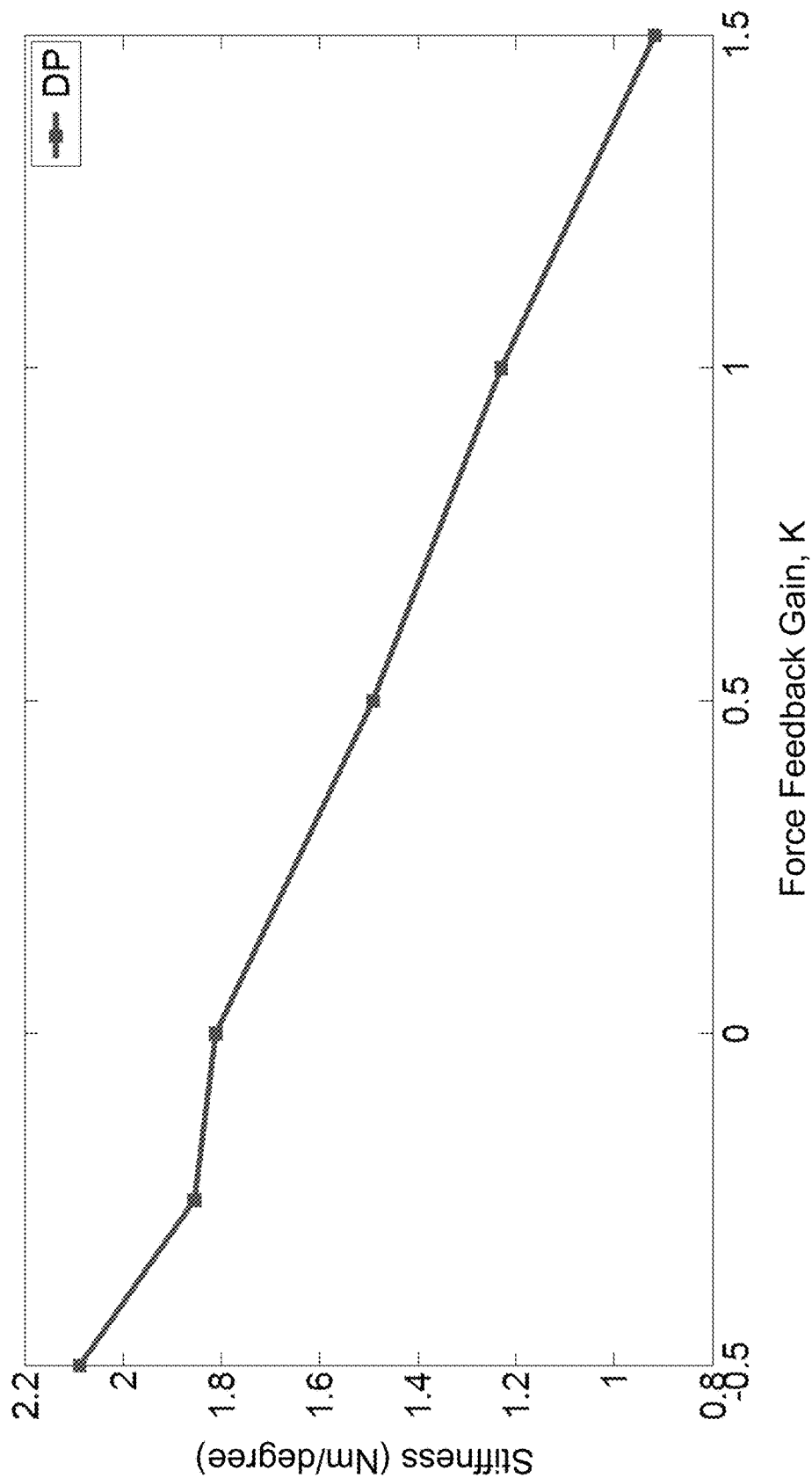
FIG. 10 is a graphical representation of ankle stiffness in DP at different feedback gains sensed according to the present disclosure.

The slopes of the best fit lines of FIG. 9 were plotted against their respective gains, as shown in FIG. 10. It can be seen that there is a near-linear relationship between the change in torque feedback gain and the quasi-static impedance (stiffness) of the prosthesis with positive gains. The stiffness of the prosthesis in DP was found to be 2.09 Nm/degree with a −0.5 gain, that decreased to 0.92 Nm/degree with a gain of 1.5.

Inversion-Eversion Stiffness

To test the IE stiffness, six tests were performed with torque feedback gains having a range of −0.5 to 1.5. In each test, the Ankelbot moved the foot to 12 eversion from the equilibrium point, and in continuous motion returned the foot to 12 inversion. Large angular displacements were needed in the IE test because the ankle-foot prosthesis shows a smaller passive stiffness in IE than in DP.

Figure 11:
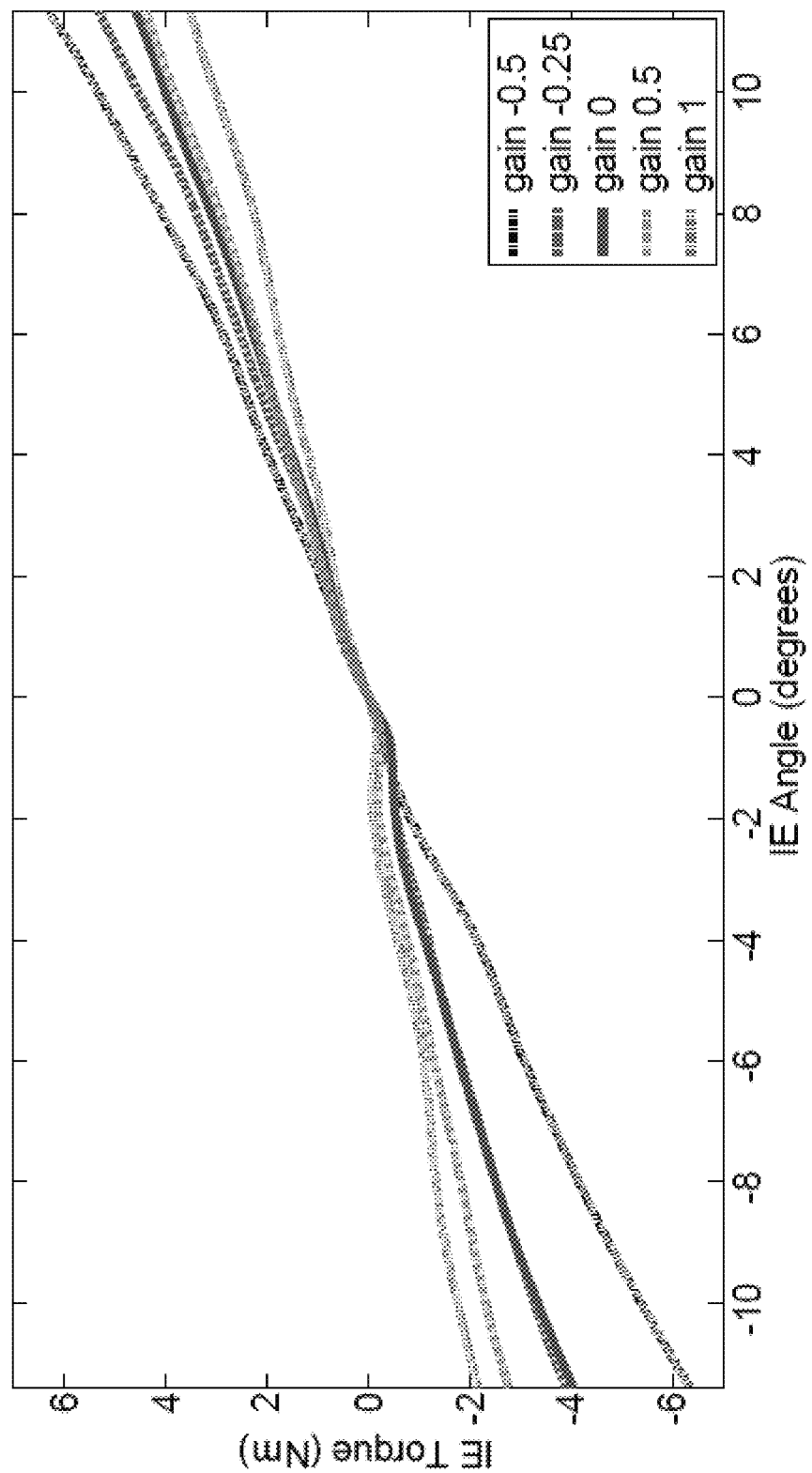
FIG. 11 is a graphical representation of IE angle and torque at different feedback gains sensed according to the present disclosure.

It can be seen in FIG. 11 that the change in feedback gain effectively changed the stiffness of the ankle in IE. Similar to the DP test, negative gains caused the prosthesis stiffness to increase when compared to zero gain. With positive gains, the prosthesis stiffness decreased with respect to zero gain. All the gains produced near-linear changes in IE torque with respect to the change in angle, with some deviation near the origin caused by transition in the ankle from loading to unloading.

Figure 12:
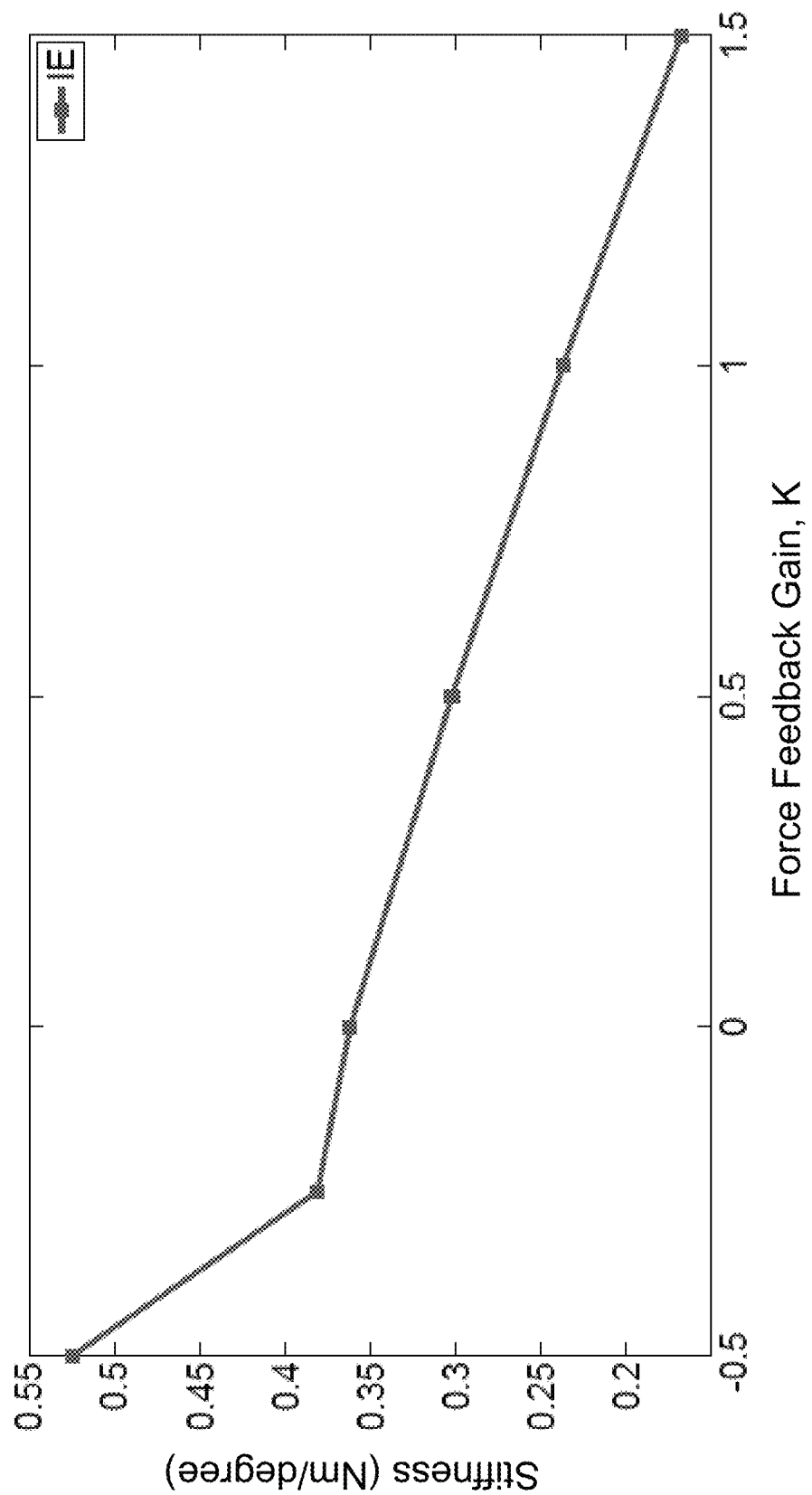
FIG. 12 is a graphical representation of ankle stiffness in IE at different feedback gains sensed according to the present disclosure.

The quasi-static impedance (stiffness) of the ankle was plotted against their respective gains, as shown in FIG. 12. This plot indicates a near-linear relationship between the change in torque feedback gain and the quasi-static impedance (stiffness) of the prosthesis for the positive gain. The prosthesis stiffness in IE was found to be 0.53 Nm/degree at a −0.5 gain that decreased to 0.17 Nm/degree at gain 1.5.

Example 6—Controller Evaluation 2

Test Setup

To evaluate the ankle-foot robot, a circular treadmill was developed, allowing the ankle-foot robot to be examined while walking in a turning pattern without the need of human interaction. The circular treadmill was composed of a wooden disk with a 1 meter radius. 8 coaster wheels were connected to the outside lower edge of the disk for weight bearing, and a turn table was connected in the center of the disk to bear weight and to constrain the disk from sliding on the horizontal plane.

A motor and planetary gear box powered the rotation of the disk. The prosthetic rob was connected to a horizontal bar by a universal joint which acted as a passive knee. The bar had one end connected to a pivot, and a second end connected to a cable connected to a motor and a gear box which could raise and lower the bar and robot. The second end of the bar was also connected to a weight which was supported by the prosthetic leg when the bar was lowered or by the motor and gear box when the bar was raised. The prosthetic leg, bar, motor and gear box, and weight were attached to an aluminum frame, which was not coupled to the treadmill except when the foot contacted the wooden disk.

The platform could lift and lower the foot and apply weight to emulate a human walk. The radius of the turn of each step could be increased or decreased by sliding the frame so the foot was closer to or farther away from the center of the treadmill. The weight supported by the prosthetic leg could also be controlled by adding or removing weights, or by sliding the joint closer to or farther away from the weight.

The speed of the treadmill disk was controlled using an open loop controller. The final gear ratio was 341:1, resulting in a maximum walking speed of 1.63 meters/second (m/s), a speed greater than the average preferred human walking speed of 1.30 m/s. The lifting mechanism used a PD controller with feedback from a quadrature encoder, and the input was a sine wave with the same frequency as the gait. The frequency of the sine wave and the gait were synchronized using a finite-state machine. The amplitude and time shift of the sine wave were dependent on the prosthetic ankle-foot tuning, the amount of weight being used, and the position of the prosthesis with respect to the frame and treadmill.

The lifting mechanism was capable of lifting 118 kg at 10.6 m/s, although the weight supported by the prosthetic leg was higher and depended on the position of the shank of the robot with respect to the horizontal bar.

Prosthesis and Controller Performance Evaluation

The circular treadmill was used to test the prosthesis performance with the impedance/admittance control and to compare the results with the performance of the device using a position control. The impedance/admittance controller was set with a torque feedback gain of 0.5 for both DP and IE, and the foot was subjected to a 23 kg load. The position controller used a PD controller to follow the trajectory of the previously recorded data of a human subject ankle in both DP and IE.

Figure 13A:
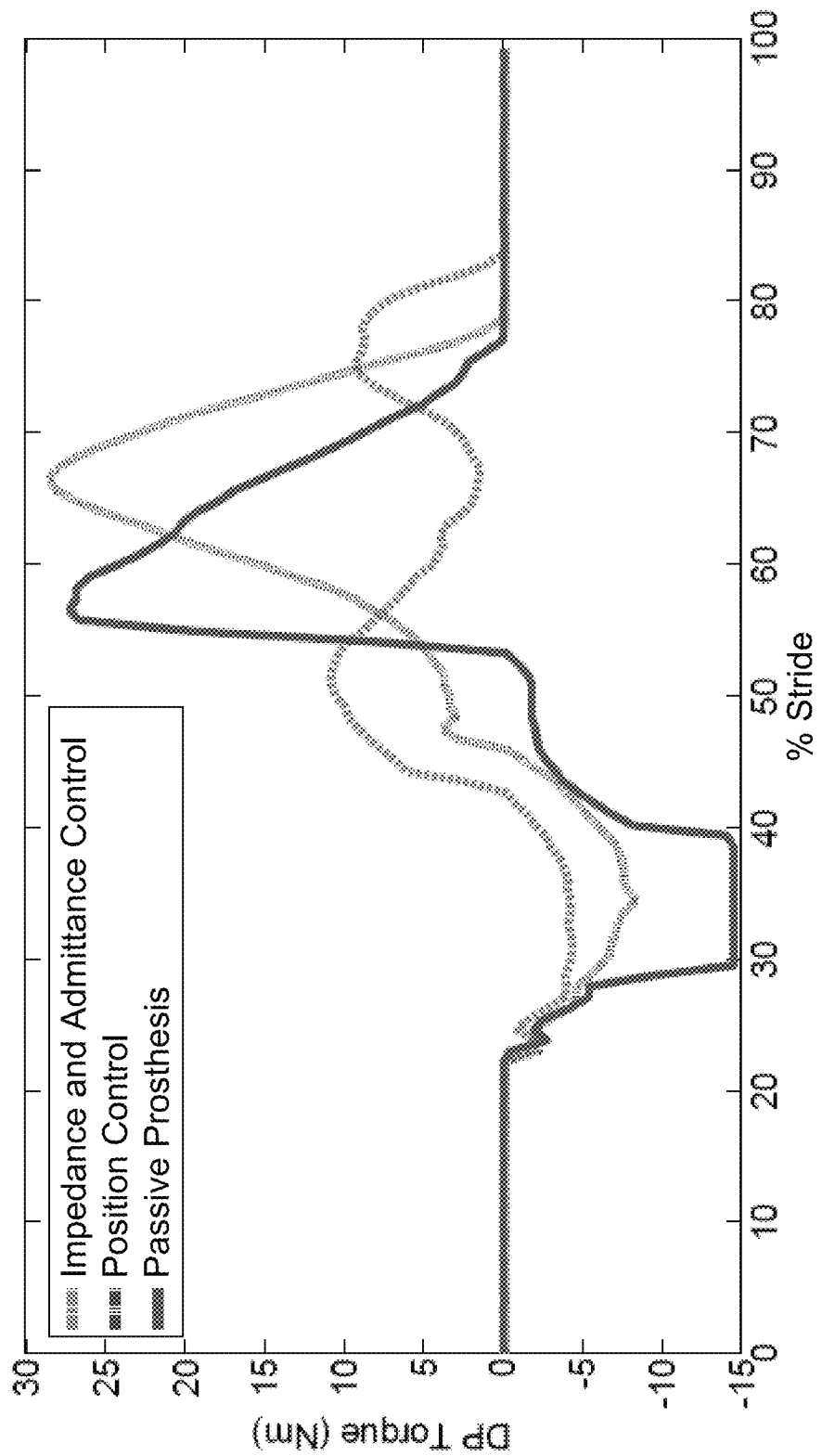
FIG. 13A is a graphical representation of ankle external torque in DP during a representative gait cycle with different control strategies.
Figure 13B:
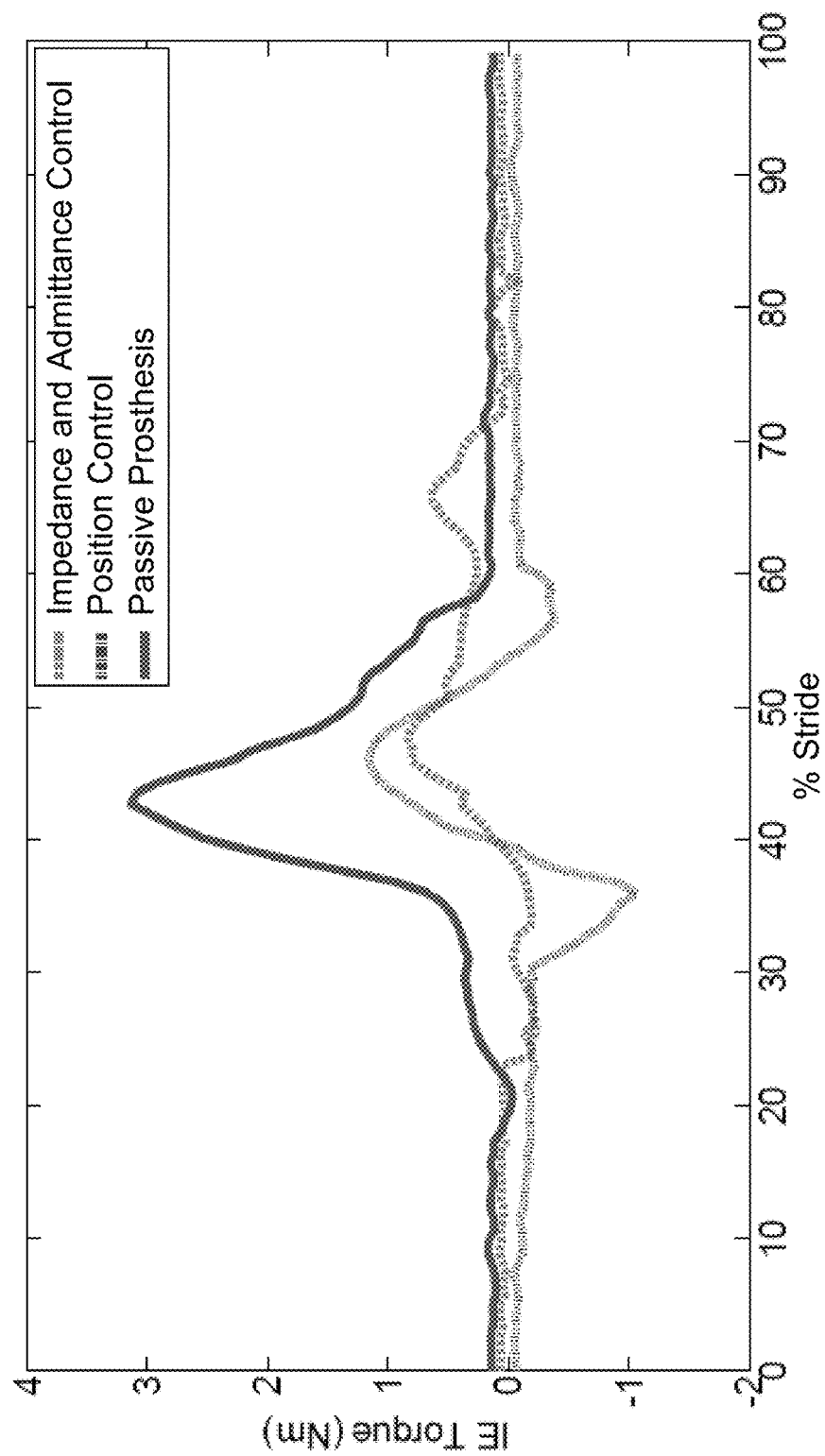
FIG. 13B is a graphical representation of ankle external torque in IE during a representative gait cycle with different control strategies.

With all controls off, the prosthesis behaved as a passive prosthesis with the stiffness equivalent to gain zero as shown in FIGS. 13A and 13B. During the tests the ground reaction torques at the foot were obtained from the strain gauge readings. It was seen that during the swing phase, there were zero torque feedbacks because the foot was not in contact with the ground. When contact with the ground occurred, the passive prosthesis showed the largest reaction torques, which saturated the data acquisition system equivalent to 15 Nm torque.

The position controller decreased the DP torque at heel-strike, but showed similar torque at push-off when compared to the passive prosthesis. The impedance/admittance controller showed the least amount of DP torques both at heel-strike and push-off. IE torques were the largest in the passive prosthesis and the impedance/admittance controller showed the least amount of torque. Inversion torques were larger for all experiments which is expected as the foot is turning left as it walks on the treadmill, putting pressure on the inside edge of the foot.

Referring again to FIG. 13A and FIG. 13B, it can be seen that the impedance/admittance controller was capable of reducing the amount of external torque in the foot in both DP and IE, however it increased the amount of time the foot was in contact with the ground. The impedance controller is effectively changing the stiffness of the ankle by applying a torque in the same direction as the disturbance torque. This causes the foot to be at a larger dorsiflexion angle compared to the reference input, resulting in extended time for push-off.

Figure 14A:
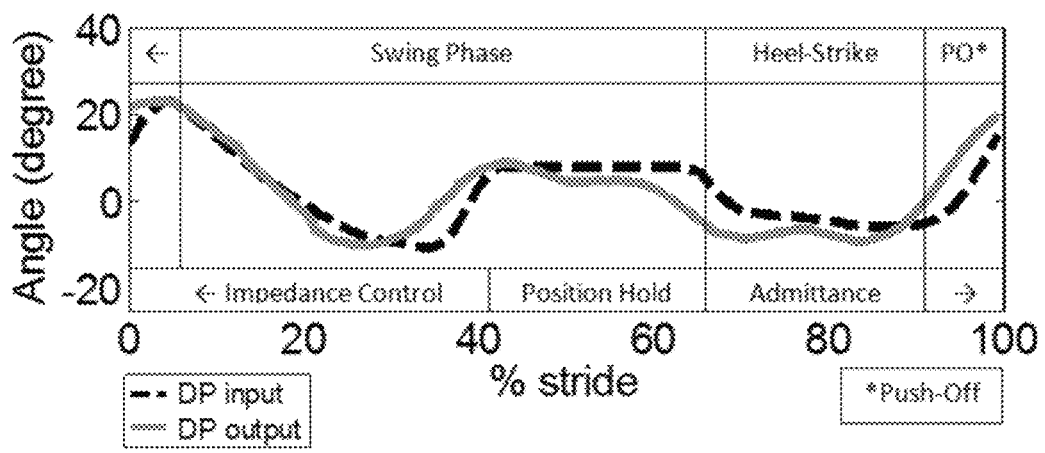
FIG. 14A is a graphical representation of an input and an output of the prosthesis' ankle trajectory in DP during a representative gait cycle with admittance and impedance control.
Figure 14B:
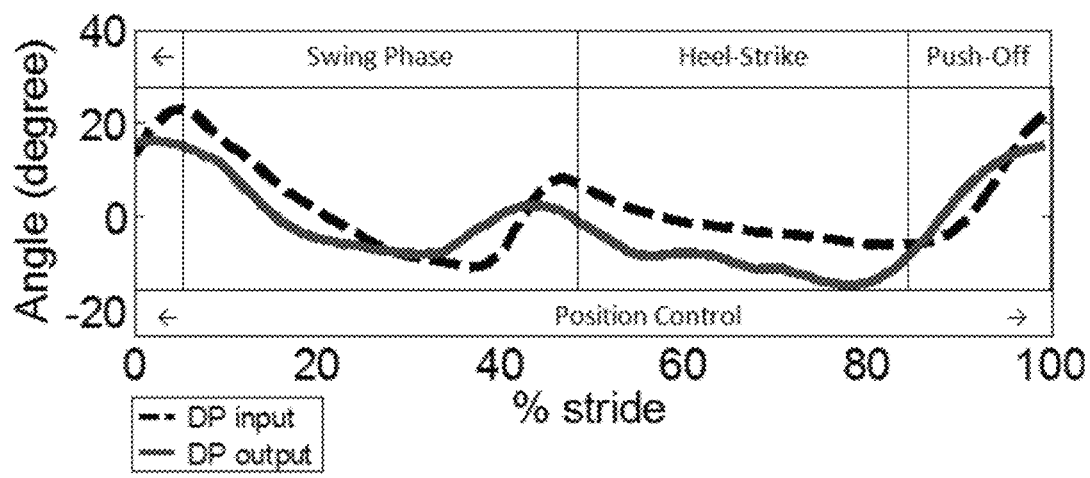
FIG. 14B is a graphical representation of an input and an output of the prosthesis' ankle trajectory in DP during a representative gait cycle with position control.
Figure 15A:
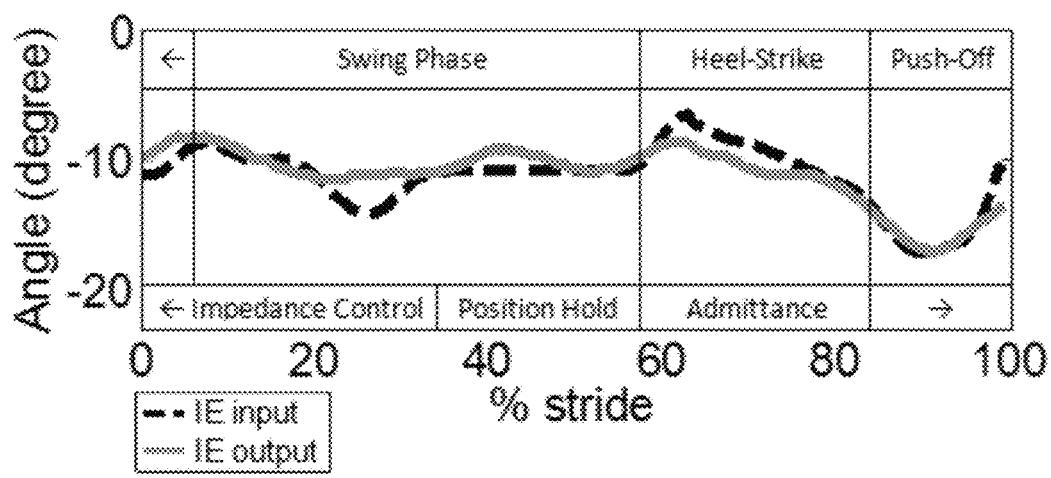
FIG. 15A is a graphical representation of an input and an output of the prosthesis' ankle trajectory in IE during a representative gait cycle with admittance and impedance control.
Figure 15B:
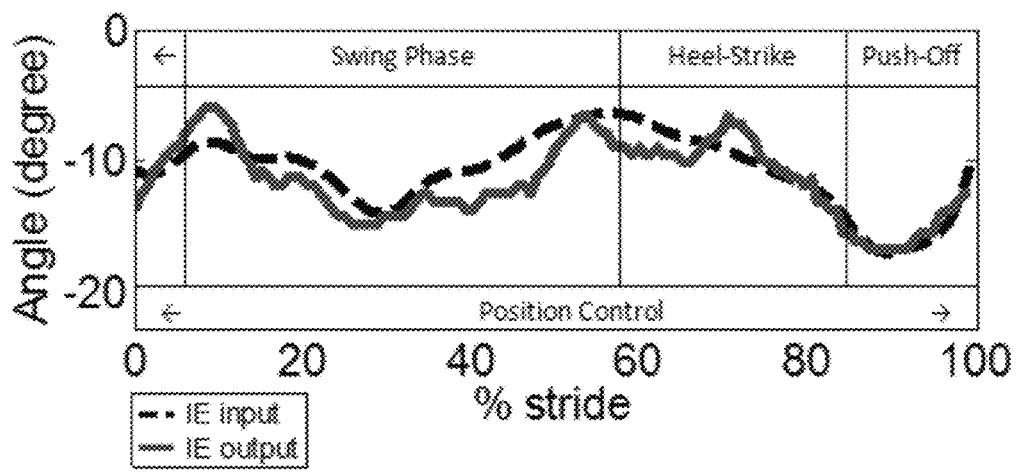
FIG. 15B is a graphical representation of an input and an output of the prosthesis' ankle trajectory in IE during a representative gait cycle with position control.

The input and output trajectories of the foot in both DP and IE during the tests can be seen in FIGS. 14A,B and FIGS. 15A,B, respectively. The input data is the time history of rotations of a human ankle during gait, and the output plots have a time shift to remove the 75 milliseconds delay of output. It can be seen that the impedance and admittance controller input held the ankle constant for about 40% to 65% of the stride, due to the state machine reaching the index of the expected heel-strike without a heel-strike occurring. The impedance/admittance controller was capable of tracking the reference trajectory compared to the position control, because it accounts for the external torques in the control.

The tests with the circular treadmill showed that the impedance/admittance controller were capable of better tracking the desired reference trajectory while decreasing the maximum reaction torques in the foot. In both DP and IE directions, the external torques at both heel-strike and push-off were greatly reduced. In IE, an increased external inversion torque was developed due to constraints imposed by the turning disk, and the impedance control was capable of accommodating and reducing this external torque. The finite state machine was capable of properly switching to admittance control at heel-strike, and back to impedance control at push-off. In addition, the finite-state machine was capable of adjusting the stride duration by adjusting the foot to the heel-strike angle, and holding the position until heel-strike was detected.

Controller Evaluation with Bowden Cables

To evaluate the impedance/admittance controller in relation to a configuration of the prosthesis using Bowden cables, the pre-recorded data of the ankle kinematics of a human subject during a step turn was used as an input. The ankle rotations were recorded using a motion capture camera system (OptiTrack Prime 17W). The controllers used the pre-recorded human motion to adjust the neutral position of the ankle and position feedback from quadrature encoders mounted on each motor to estimate the appropriate motor inputs using PD controllers. For a first motor controller, the input reference angle was the sum of the DP and IE angles. For a second motor controller, the reference angle was the difference between the DP and IE angles.

The ankle-foot prosthesis was capable of mimicking the recorded human ankle motion in both frontal and sagittal planes. FIGS. 16A,B show the input reference angle and the output trajectories that followed closely to the human ankle rotations, indicating a plausible kinematics design. The system showed a 40 ms delay between the input and output which was removed for ease of comparison.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

The invention claimed is:

1. A prosthesis comprising:
    a coupling configured to engage a residual limb of a subject;
    a shaft having a first end connected to the coupling and an opposing second end;
    a foot piece connected to the second end of the shaft, the foot piece comprising an ankle plate and a sole piece configured to contact a surface, the ankle plate including a rear and a front;
    a first drum;
    a second drum; and
    a cable coupled to (i) the rear of the ankle plate (ii) the front of the ankle plate, (iii) the first drum, and (iv) the second drum, the cable running sequentially from (a) the rear of the ankle plate (b) to the first drum (c) to the front of the ankle plate (d) to the second drum (e) to the rear of the ankle plate, and
    wherein a position of the ankle plate is configured to have at least two degrees of freedom about a joint of the foot piece.

2. The prosthesis of claim 1, wherein the position of the ankle plate can adapt to the surface in dorsiflexion-plantarflexion directions and inversion-eversion directions.

3. The prosthesis of claim 1, wherein the joint is configured to transmit rotary motion in a transverse plane, the joint including an elastomer to provide a constant passive stiffness to the ankle plate.

4. The prosthesis of claim 1, wherein the ankle plate is one of a carbon-fiber plate or a fiberglass-composite plate.

5. The prosthesis of claim 1, which includes an ankle plate pulley positioned on the front of the ankle plate, and wherein the cable runs from the rear of the ankle plate, to the first drum, through a track of the ankle plate pulley, to the second drum, to the rear of the ankle plate.

6. A prosthesis comprising:
a coupling configured to engage a residual limb of a subject;
a shaft having a first end connected to the coupling and an opposing second end;
a foot piece connected to the second end of the shaft, the foot piece comprising an ankle plate and a sole piece configured to contact a surface;
at least one computer configured to detect a state of the foot piece and to transmit an indication of the state of the foot piece; and
a motor assembly including a first motor, a second motor, a first drum, a second drum and a cable, the cable coupled to (i) a rear of the ankle plate, (ii) a front of the ankle plate, (iii) the first drum, and (iv) the second drum and running sequentially from (a) the rear of the ankle plate (b) to the first drum (c) to the front of the ankle plate (d) to the second drum (e) to the rear of the ankle plate, and wherein the motor assembly is configured to receive the indication of the state of the foot piece and to control a position of the ankle plate about a joint of the foot piece in at least two degrees of freedom based on the state of the foot piece using the first and second motors.

7. The prosthesis of claim 6, wherein the state of the foot piece is dependent on a phase of a gait of the subject, and wherein the phase of the gait of the subject is one of heel-strike, foot-flat, and toe-off.

8. The prosthesis of claim 7, wherein the computer includes at least one of an impedance controller and an admittance controller.

9. The prosthesis of claim 8, wherein the admittance controller is activated during heel-strike, and the impedance controller is activated during foot-flat and toe-off.

10. The prosthesis of claim 6, wherein the motor assembly further comprises first and second gearboxes.

11. The prosthesis of claim 10, wherein the position of the ankle plate is controlled by the cable.

12. The prosthesis of claim 11, wherein the cable is a Bowden cable.

13. The prosthesis of claim 12, wherein the Bowden cable allows for the motor assembly to be placed in a location alternative to the shaft.

14. The prosthesis of claim 6, wherein the joint is configured to transmit rotary motion in a transverse plane, the joint including an elastomer to provide a constant passive stiffness to the ankle plate.

15. The prosthesis of claim 6, further comprising
a plurality of torque sensors disposed within the prosthesis and configured to transmit torque feedback; and
a finite state machine connected to the at least one computer and configured to receive the torque feedback and to transmit a desired trajectory to the motor assembly.

16. The prosthesis of claim 6, wherein the ankle plate is one of a carbon-fiber plate or a fiberglass-composite plate.

17. The prosthesis of claim 6, which includes an ankle plate pulley positioned on the front of the ankle plate, and wherein the cable runs from the rear of the ankle plate, to the first drum, through a track of the ankle plate pulley, to the second drum, to the rear of the ankle plate.

18. The prosthesis of claim 17, wherein the motor assembly further includes a front pair of pulleys and a rear pair of pulleys, and wherein the cable runs from the rear of the ankle plate, through a track of a first one of the back pair of pulleys, through a track of a first one of the front pair of pulleys, through the track of the ankle plate pulley, through a track of a second one of the front pair of pulleys, through a track of a second one of the back pair of pulleys, to the rear of the ankle plate.

19. The prosthesis of claim 6, wherein the motor assembly further includes a front pair of pulleys and a rear pair of pulleys, the cable running sequentially through (a) a track of a first one of the back pair of pulleys, (b) a track of a first one of the front pair of pulleys, (c) a track of a second one of the front pair of pulleys, and (d) a track of a second one of the back pair of pulleys.

20. The prosthesis of claim 6, wherein the motor assembly is configured to receive the indication of the state of the foot piece and to control the position of the ankle plate (i) through Dorsiflexion-Platarflexion motion by rotating the first and second motors in a same direction, and (ii) through Inversion-Eversion motion by rotating the first and second motors in opposite directions.

21. The prosthesis of claim 6, wherein the motor assembly further includes a first gearbox and a second gear box operatively coupled to the first and second motors, respectively.

* * * * *